US010219857B2

(12) United States Patent
Sherman et al.

(10) Patent No.: US 10,219,857 B2
(45) Date of Patent: Mar. 5, 2019

(54) RF ENERGY DELIVERY SYSTEM

(71) Applicant: Medtronic Ablation Frontiers LLC, Minneapolis, MN (US)

(72) Inventors: Marshall L. Sherman, Cardiff by the Sea, CA (US); Randell L. Werneth, San Diego, CA (US); J. Christopher Flaherty, Topsfield, MA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1303 days.

(21) Appl. No.: 14/297,088

(22) Filed: Jun. 5, 2014

(65) Prior Publication Data

US 2014/0288546 A1  Sep. 25, 2014

Related U.S. Application Data

(62) Division of application No. 12/117,596, filed on May 8, 2008, now Pat. No. 8,771,269.

(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00214* (2013.01);
(Continued)

(58) Field of Classification Search
CPC ... A61B 17/128; A61B 17/28; A61B 17/2812; A61B 18/1442; A61B 2017/0023;
(Continued)

(56) References Cited

U.S. PATENT DOCUMENTS 3,516,412 A    6/1970  Ackerman
3,614,478 A *  10/1971 Schiff ................ A61B 5/04004
                                                327/555
(Continued)

FOREIGN PATENT DOCUMENTS

AU   5200671   10/2005
CA   2327322   11/1999
(Continued)

OTHER PUBLICATIONS

Oral et al., "Catheter ablation for paroxysmal artrial fibrillation: segmental pulmonary vein ostial ablation versus left atrial ablation," Circulation, vol. 108, pp. 2355-2360, 2003.
(Continued)

*Primary Examiner* — Michael Peffley
*Assistant Examiner* — Amanda Zink
(74) *Attorney, Agent, or Firm* — Christopher & Weisberg, P.A.

(57) ABSTRACT

A radio frequency tissue ablation system with a radio frequency generator, the generator comprising a radio frequency source, at least four independently controllable radio frequency outputs, a user interface and a controller configured to delivery radio frequency energy from the radio frequency source to the radio frequency outputs in one of at least two different output configurations in response to a configuration selection made through the user.

20 Claims, 21 Drawing Sheets

Related U.S. Application Data

(60) Provisional application No. 60/928,788, filed on May 11, 2007.

(52) U.S. Cl.
CPC ............... *A61B 2018/00375* (2013.01); *A61B 2018/1407* (2013.01); *A61B 2018/1467* (2013.01); *A61B 2018/1475* (2013.01)

(58) Field of Classification Search
CPC ........... A61B 2018/00077; A61B 2018/00928; A61B 2018/1495
See application file for complete search history.

(56) References Cited

U.S. PATENT DOCUMENTS

| | | |
|---|---|---|
| 3,951,136 A | 4/1976 | Wall |
| 4,017,903 A | 4/1977 | Chu |
| 4,112,952 A | 9/1978 | Thomas et al. |
| 4,411,266 A | 10/1983 | Cosman |
| 4,432,377 A | 2/1984 | Dickhudt |
| 4,660,571 A | 4/1987 | Hess et al. |
| 4,785,815 A | 11/1988 | Cohen |
| 4,860,769 A | 8/1989 | Fogarty et al. |
| 4,869,248 A | 9/1989 | Narula |
| 4,882,777 A | 11/1989 | Narula |
| 4,896,671 A | 1/1990 | Cunningham et al. |
| 4,907,589 A | 3/1990 | Cosman |
| 4,920,980 A | 5/1990 | Jackowski |
| 4,940,064 A | 7/1990 | Desai |
| 4,966,597 A | 10/1990 | Cosman |
| 5,010,894 A | 4/1991 | Edhag |
| 5,016,808 A | 5/1991 | Heil, Jr. et al. |
| 5,083,565 A | 1/1992 | Parins |
| 5,100,423 A | 3/1992 | Fearnot |
| 5,156,151 A | 10/1992 | Imran |
| 5,184,621 A | 2/1993 | Vogel et al. |
| 5,215,103 A | 6/1993 | Desai |
| 5,228,442 A | 7/1993 | Imran |
| 5,230,349 A | 7/1993 | Langberg |
| 5,231,987 A | 8/1993 | Robson |
| 5,231,995 A | 8/1993 | Desai |
| 5,234,004 A | 8/1993 | Hascoet et al. |
| 5,239,999 A | 8/1993 | Imran |
| 5,255,679 A | 10/1993 | Imran |
| 5,279,299 A | 1/1994 | Imran |
| 5,281,213 A | 1/1994 | Milder et al. |
| 5,281,218 A | 1/1994 | Imran |
| 5,309,910 A | 5/1994 | Edwards et al. |
| 5,313,943 A | 5/1994 | Houser et al. |
| 5,318,525 A | 6/1994 | West et al. |
| 5,324,284 A | 6/1994 | Imran |
| 5,327,889 A | 7/1994 | Imran |
| 5,330,466 A | 7/1994 | Imran |
| 5,334,193 A | 8/1994 | Nardella |
| 5,341,295 A | 8/1994 | Imran |
| 5,342,357 A | 8/1994 | Nardella |
| 5,345,936 A | 9/1994 | Pomeranz et al. |
| 5,348,554 A | 9/1994 | Imran et al. |
| D351,652 S | 10/1994 | Thompson et al. |
| 5,346,352 A | 11/1994 | Cimino et al. |
| 5,365,926 A | 11/1994 | Desai |
| 5,370,644 A | 12/1994 | Langberg |
| 5,383,917 A | 1/1995 | Desai et al. |
| 5,391,147 A | 2/1995 | Imran et al. |
| 5,397,304 A | 3/1995 | Truckai |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,411,025 A | 5/1995 | Webster, Jr. |
| 5,423,808 A | 6/1995 | Edwards et al. |
| 5,423,811 A | 6/1995 | Imran et al. |
| 5,425,704 A * | 6/1995 | Sakurai ............... A61B 8/546 310/316.01 |
| 5,433,198 A | 7/1995 | Desai |
| 5,433,739 A | 7/1995 | Sluijter et al. |
| 5,445,148 A | 8/1995 | Jaraczewski et al. |
| 5,462,521 A | 10/1995 | Brucker et al. |
| 5,462,545 A | 10/1995 | Wang et al. |
| 5,465,717 A | 11/1995 | Imran et al. |
| 5,471,982 A | 12/1995 | Edwards et al. |
| 5,487,757 A | 1/1996 | Truckai et al. |
| 5,492,119 A | 2/1996 | Abrams |
| 5,500,011 A | 3/1996 | Desai |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,536,267 A | 7/1996 | Edwards et al. |
| 5,540,681 A | 7/1996 | Strul et al. |
| 5,545,191 A | 8/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,573,533 A | 11/1996 | Strul |
| 5,575,766 A | 11/1996 | Swartz et al. |
| 5,575,810 A | 11/1996 | Swanson et al. |
| 5,578,007 A | 11/1996 | Imran |
| 5,582,609 A | 12/1996 | Swanson et al. |
| 5,584,830 A | 12/1996 | Ladd et al. |
| 5,588,432 A | 12/1996 | Crowley |
| 5,588,964 A | 12/1996 | Imran et al. |
| 5,595,183 A | 1/1997 | Swanson et al. |
| 5,596,995 A | 1/1997 | Sherman et al. |
| 5,598,848 A | 2/1997 | Swanson et al. |
| 5,601,088 A | 2/1997 | Swanson et al. |
| 5,606,974 A | 3/1997 | Castellano et al. |
| 5,607,462 A | 3/1997 | Imran |
| 5,620,481 A | 4/1997 | Desai et al. |
| 5,626,136 A | 5/1997 | Webster, Jr. |
| 5,630,425 A | 5/1997 | Panescu et al. |
| 5,630,837 A | 5/1997 | Crowley |
| 5,637,090 A | 6/1997 | McGee et al. |
| D381,076 S | 7/1997 | Thornton et al. |
| 5,645,064 A | 7/1997 | Littmann et al. |
| 5,645,082 A | 7/1997 | Sung et al. |
| 5,656,029 A | 8/1997 | Imran et al. |
| 5,657,755 A | 8/1997 | Desai |
| 5,658,278 A | 8/1997 | Imran et al. |
| 5,662,606 A | 9/1997 | Cimino et al. |
| 5,666,970 A | 9/1997 | Smith |
| 5,673,695 A | 10/1997 | McGee et al. |
| 5,680,860 A | 10/1997 | Imran |
| 5,681,280 A | 10/1997 | Rusk et al. |
| 5,682,885 A | 11/1997 | Littmann et al. |
| 5,685,322 A | 11/1997 | Sung |
| 5,687,723 A | 11/1997 | Avitall |
| 5,693,078 A | 12/1997 | Desai |
| 5,697,927 A | 12/1997 | Imran et al. |
| 5,697,928 A | 12/1997 | Walcott et al. |
| 5,699,796 A | 12/1997 | Littmann et al. |
| 5,702,438 A | 12/1997 | Avitall |
| 5,704,791 A | 1/1998 | Gillio |
| 5,706,809 A | 1/1998 | Littmann et al. |
| 5,711,298 A | 1/1998 | Littmann et al. |
| 5,716,389 A | 2/1998 | Walinsky et al. |
| 5,722,975 A | 3/1998 | Edwards et al. |
| 5,724,985 A | 3/1998 | Snell et al. |
| 5,733,323 A | 3/1998 | Buck et al. |
| 5,735,280 A | 4/1998 | Sherman et al. |
| 5,741,320 A | 4/1998 | Thornton et al. |
| 5,766,152 A | 6/1998 | Morley et al. |
| 5,769,791 A | 6/1998 | Benaron et al. |
| 5,769,847 A | 6/1998 | Panescu et al. |
| 5,772,590 A | 6/1998 | Webster, Jr. |
| 5,775,327 A | 7/1998 | Randolph et al. |
| 5,782,239 A | 7/1998 | Webster, Jr. |
| 5,782,760 A | 7/1998 | Schaer |
| 5,782,828 A | 7/1998 | Chen et al. |
| 5,782,899 A | 7/1998 | Imran |
| 5,792,140 A | 8/1998 | Tu et al. |
| 5,800,482 A | 9/1998 | Pomeranz et al. |
| 5,810,740 A | 9/1998 | Painser |

(56) References Cited

U.S. PATENT DOCUMENTS

| | | |
|---|---|---|
| 5,820,568 A | 10/1998 | Willis |
| 5,827,272 A | 10/1998 | Breining et al. |
| 5,837,001 A | 11/1998 | Mackey |
| 5,849,028 A | 12/1998 | Chen |
| 5,857,464 A | 1/1999 | Desai |
| 5,857,997 A | 1/1999 | Cimino et al. |
| 5,860,920 A | 1/1999 | McGee et al. |
| 5,863,291 A | 1/1999 | Schaer |
| 5,871,523 A | 2/1999 | Fleishman et al. |
| 5,873,865 A | 2/1999 | Horzewski et al. |
| 5,876,399 A | 3/1999 | Chia et al. |
| 5,881,732 A | 3/1999 | Sung et al. |
| 5,882,333 A | 3/1999 | Schaer et al. |
| 5,885,278 A | 3/1999 | Fleishman |
| 5,891,027 A | 4/1999 | Tu et al. |
| 5,891,135 A | 4/1999 | Jackson et al. |
| 5,891,137 A | 4/1999 | Chia et al. |
| 5,891,138 A | 4/1999 | Tu et al. |
| 5,893,847 A | 4/1999 | Kordis |
| 5,893,884 A | 4/1999 | Tu |
| 5,893,885 A | 4/1999 | Webster, Jr. |
| 5,895,355 A | 4/1999 | Schaer |
| 5,895,417 A | 4/1999 | Pomeranz et al. |
| 5,897,554 A | 4/1999 | Chia et al. |
| 5,904,680 A | 5/1999 | Kordis et al. |
| 5,906,605 A | 5/1999 | Coxum |
| 5,910,129 A | 6/1999 | Koblish et al. |
| 5,911,720 A | 6/1999 | Bourne et al. |
| 5,913,854 A | 6/1999 | Maguire et al. |
| 5,916,214 A | 6/1999 | Cosio et al. |
| 5,928,191 A | 7/1999 | Houser et al. |
| 5,931,835 A | 8/1999 | Mackey |
| 5,935,063 A | 8/1999 | Nguyen |
| 5,938,694 A | 8/1999 | Jaraczewski et al. |
| 5,941,845 A | 8/1999 | Tu et al. |
| 5,951,471 A | 9/1999 | de la Rama et al. |
| 5,954,719 A | 9/1999 | Chen et al. |
| 5,957,842 A | 9/1999 | Littmann et al. |
| 5,960,796 A | 10/1999 | Sung et al. |
| 5,967,978 A | 10/1999 | Littmann et al. |
| 5,968,040 A | 10/1999 | Swanson et al. |
| 5,971,980 A | 10/1999 | Sherman |
| 5,992,418 A | 11/1999 | de la Rama et al. |
| 5,997,532 A | 12/1999 | McLaughlin et al. |
| 6,001,093 A | 12/1999 | Swanson et al. |
| 6,001,095 A | 12/1999 | de la Rama et al. |
| 6,002,956 A | 12/1999 | Schaer |
| 6,004,269 A | 12/1999 | Crowley et al. |
| 6,014,581 A | 1/2000 | Whayne et al. |
| 6,021,340 A | 2/2000 | Randolph et al. |
| 6,023,638 A | 2/2000 | Swanson |
| 6,029,091 A | 2/2000 | de la Rama et al. |
| 6,032,674 A | 3/2000 | Eggers et al. |
| 6,033,403 A | 3/2000 | Tu et al. |
| 6,042,580 A | 3/2000 | Simpson |
| 6,045,550 A | 4/2000 | Simpson et al. |
| 6,048,329 A | 4/2000 | Thompson et al. |
| 6,049,737 A | 4/2000 | Simpson et al. |
| 6,050,994 A | 4/2000 | Sherman |
| 6,052,612 A | 4/2000 | Desai |
| 6,053,937 A | 4/2000 | Edwards et al. |
| 6,056,744 A | 5/2000 | Edwards |
| 6,059,778 A | 5/2000 | Sherman |
| 6,063,077 A | 5/2000 | Schaer |
| 6,063,082 A | 5/2000 | DeVore et al. |
| 6,064,902 A | 5/2000 | Haissaguerre et al. |
| 6,068,629 A | 5/2000 | Haissaguerre et al. |
| 6,070,094 A | 5/2000 | Swanson et al. |
| 6,071,274 A | 6/2000 | Thompson et al. |
| 6,071,279 A | 6/2000 | Whayne et al. |
| 6,071,281 A | 6/2000 | Burnside et al. |
| 6,071,282 A | 6/2000 | Fleishman |
| 6,074,351 A | 6/2000 | Houser |
| 6,086,581 A | 7/2000 | Reynolds et al. |
| 6,088,610 A | 7/2000 | Littmann et al. |
| 6,096,036 A | 8/2000 | Bowe et al. |
| 6,099,524 A | 8/2000 | Lipson et al. |
| 6,106,522 A | 8/2000 | Fleischman et al. |
| 6,107,699 A | 8/2000 | Swanson |
| 6,115,626 A | 9/2000 | Whayne et al. |
| 6,119,041 A | 9/2000 | Pomeranz et al. |
| 6,120,476 A | 9/2000 | Fung et al. |
| 6,129,724 A | 10/2000 | Fleischman et al. |
| 6,141,576 A | 10/2000 | Littmann et al. |
| 6,146,379 A | 11/2000 | Fleischman et al. |
| 6,146,381 A | 11/2000 | Bowe et al. |
| 6,165,169 A | 12/2000 | Panescu et al. |
| 6,167,291 A | 12/2000 | Barajas et al. |
| 6,171,305 B1 | 1/2001 | Sherman |
| 6,171,306 B1 | 1/2001 | Swanson et al. |
| 6,179,833 B1 | 1/2001 | Taylor |
| 6,200,314 B1 | 3/2001 | Sherman |
| 6,212,426 B1 | 4/2001 | Swanson et al. |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,573 B1 | 4/2001 | Webster |
| 6,217,576 B1 | 4/2001 | Tu et al. |
| 6,226,542 B1 | 5/2001 | Reisfeld |
| 6,238,390 B1 | 5/2001 | Tu et al. |
| 6,241,666 B1 | 6/2001 | Pomeranz et al. |
| 6,241,724 B1 | 6/2001 | Fleischman et al. |
| 6,241,725 B1 | 6/2001 | Cosman |
| 6,241,726 B1 | 6/2001 | Raymond et al. |
| 6,241,727 B1 | 6/2001 | Tu et al. |
| 6,241,728 B1 | 6/2001 | Gaiser et al. |
| 6,241,754 B1 | 6/2001 | Swanson et al. |
| 6,245,067 B1 | 6/2001 | Tu et al. |
| 6,245,089 B1 | 6/2001 | Daniel et al. |
| 6,246,902 B1 * | 6/2001 | Naylor ................ A61B 5/0428 128/901 |
| 6,251,107 B1 | 6/2001 | Schaer |
| 6,256,540 B1 | 7/2001 | Panescu et al. |
| 6,264,664 B1 | 7/2001 | Avellanet |
| 6,267,746 B1 | 7/2001 | Bumbalough |
| 6,290,697 B1 | 9/2001 | Tu et al. |
| 6,293,943 B1 | 9/2001 | Panescu et al. |
| 6,302,880 B1 | 10/2001 | Schaer |
| 6,309,385 B1 | 10/2001 | Simpson |
| 6,312,425 B1 | 11/2001 | Simpson et al. |
| 6,319,251 B1 | 11/2001 | Tu et al. |
| 6,325,797 B1 | 12/2001 | Stewart et al. |
| 6,332,880 B1 | 12/2001 | Yang et al. |
| 6,332,881 B1 | 12/2001 | Carner et al. |
| 6,346,104 B2 | 2/2002 | Daly et al. |
| 6,353,751 B1 | 3/2002 | Swanson |
| 6,360,128 B2 | 3/2002 | Kordis et al. |
| 6,370,435 B2 | 4/2002 | Panescu et al. |
| 6,371,955 B1 | 4/2002 | Fuimaono et al. |
| 6,379,352 B1 | 4/2002 | Reynolds et al. |
| 6,389,311 B1 | 5/2002 | Whayne et al. |
| 6,391,024 B1 | 5/2002 | Sun et al. |
| 6,398,779 B1 * | 6/2002 | Buysse ............... A61B 18/1445 606/34 |
| 6,425,894 B1 | 7/2002 | Brucker et al. |
| 6,428,536 B2 | 8/2002 | Panescu et al. |
| 6,428,537 B1 | 8/2002 | Swanson et al. |
| 6,440,129 B1 | 8/2002 | Simpson |
| 6,447,506 B1 | 9/2002 | Swanson et al. |
| 6,451,015 B1 | 9/2002 | Rittman, III et al. |
| 6,454,758 B1 | 9/2002 | Thompson et al. |
| 6,456,864 B1 | 9/2002 | Swanson et al. |
| 6,460,545 B2 | 10/2002 | Kordis |
| 6,471,693 B1 | 10/2002 | Carroll et al. |
| 6,471,699 B1 | 10/2002 | Fleischman et al. |
| 6,475,213 B1 | 11/2002 | Whayne et al. |
| 6,475,214 B1 | 11/2002 | Moaddeb |
| 6,477,396 B1 | 11/2002 | Mest et al. |
| 6,478,793 B1 | 11/2002 | Cosman et al. |
| 6,485,487 B1 | 11/2002 | Sherman |
| 6,487,441 B1 | 11/2002 | Swanson et al. |
| 6,488,678 B2 | 12/2002 | Sherman |
| 6,493,468 B1 | 12/2002 | Panescu et al. |
| 6,493,586 B1 | 12/2002 | Stahmann et al. |

(56) References Cited

U.S. PATENT DOCUMENTS

| | | |
|---|---|---|
| 6,500,167 B1 | 12/2002 | Webster, Jr. |
| 6,500,172 B1 | 12/2002 | Panescu et al. |
| 6,514,246 B1 | 2/2003 | Swanson et al. |
| 6,517,536 B2 | 2/2003 | Hooven et al. |
| 6,522,905 B2 | 2/2003 | Desai |
| 6,529,756 B1 | 3/2003 | Phan et al. |
| 6,540,744 B2 | 4/2003 | Hassett et al. |
| 6,542,773 B2 | 4/2003 | Dupree et al. |
| 6,544,262 B2 | 4/2003 | Fleischman |
| 6,551,271 B2 | 4/2003 | Nguyen |
| 6,554,794 B1 | 4/2003 | Meuller et al. |
| 6,558,378 B2 | 5/2003 | Sherman et al. |
| 6,565,511 B2 | 5/2003 | Panescu et al. |
| 6,569,114 B2 | 5/2003 | Ponzi et al. |
| 6,569,162 B2 | 5/2003 | He |
| 6,569,163 B2 | 5/2003 | Hata et al. |
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,616,657 B2 | 9/2003 | Simpson et al. |
| 6,625,482 B1 | 9/2003 | Panescu et al. |
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart et al. |
| 6,711,428 B2 | 3/2004 | Fulmaono et al. |
| 6,730,078 B2 | 5/2004 | Simpson et al. |
| 6,738,673 B2 | 5/2004 | Desai |
| 6,740,080 B2 | 5/2004 | Jain et al. |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,866,662 B2 | 3/2005 | Fuimaono et al. |
| 6,893,438 B2 | 5/2005 | Hall et al. |
| 6,893,439 B2 | 5/2005 | Fleischman et al. |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 12/2005 | Hill, III et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Fuimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0010392 A1* | 1/2002 | Desai .................. A61B 5/0422 600/374 |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0161422 A1 | 10/2002 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2004/0015164 A1 | 1/2004 | Fuimaono et al. |
| 2004/0082647 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Dednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfrey |
| 2004/0236324 A1 | 11/2004 | Muller et al. |
| 2004/0247164 A1 | 12/2004 | Furnish |
| 2005/0010095 A1 | 1/2005 | Stewart et al. |
| 2005/0015084 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Werneth et al. |
| 2006/0095030 A1 | 5/2006 | Avitall et al. |
| 2006/0106375 A1* | 5/2006 | Werneth ............ A61B 18/1492 606/32 |
| 2006/0111700 A1 | 5/2006 | Kunis et al. |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0122526 A1 | 6/2006 | Berenfield et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0206109 A1 | 9/2006 | Swanson |
| 2006/0241366 A1 | 10/2006 | Falwell et al. |
| 2007/0027448 A1 | 2/2007 | Paul et al. |
| 2007/0049816 A1 | 3/2007 | Damiano, Jr. et al. |

(56) References Cited

U.S. PATENT DOCUMENTS

| | | | |
|---|---|---|---|
| 2007/0083193 A1* | 4/2007 | Werneth | A61B 5/0422 606/41 |
| 2007/0083194 A1 | 4/2007 | Kunis et al. | |
| 2007/0083195 A1* | 4/2007 | Werneth | A61B 18/1492 606/41 |
| 2007/0106293 A1 | 5/2007 | Oral et al. | |
| 2010/0013484 A1* | 1/2010 | Wirtz | G01R 33/287 324/318 |
| 2010/0286690 A1* | 11/2010 | Paul | A61N 1/40 606/41 |

FOREIGN PATENT DOCUMENTS

| | | |
|---|---|---|
| CA | 2327518 | 11/1999 |
| CA | 2328064 | 11/1999 |
| CA | 2328070 | 11/1999 |
| CA | 2371935 | 12/2000 |
| CA | 2222617 C | 7/2002 |
| CA | 2437140 | 6/2004 |
| CA | 2492283 | 7/2005 |
| CA | 2194061 C | 4/2006 |
| CA | 2276755 C | 5/2006 |
| CA | 2251041 C | 6/2006 |
| EP | 4288112 B1 | 3/1995 |
| EP | 779059 A | 6/1997 |
| EP | 598742 B1 | 8/1999 |
| EP | 879016 B1 | 10/2003 |
| EP | 1360938 A1 | 11/2003 |
| EP | 1364677 A2 | 11/2003 |
| EP | 1554986 A1 | 7/2005 |
| EP | 823843 B1 | 10/2005 |
| EP | 1384445 B1 | 2/2006 |
| EP | 1169976 B1 | 4/2006 |
| EP | 14115680 B1 | 4/2006 |
| EP | 1011437 B1 | 5/2006 |
| EP | 1210021 B1 | 5/2006 |
| EP | 1658818 A1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 1750215 A1 | 2/2007 |
| EP | 957794 B1 | 7/2007 |
| JP | 2004188 A | 7/2004 |
| SU | 1512622 A1 | 10/1989 |
| SU | 1544396 A1 | 2/1990 |
| SU | 1690786 A1 | 11/1991 |
| WO | 1990006079 A1 | 6/1990 |
| WO | 1993008756 A1 | 5/1993 |
| WO | 1993025273 A1 | 12/1993 |
| WO | 1994012098 A1 | 6/1994 |
| WO | 1996010961 A1 | 4/1996 |
| WO | 1996032885 A1 | 10/1996 |
| WO | 1996032897 A1 | 10/1996 |
| WO | 1996034558 A1 | 11/1996 |
| WO | 1996034559 A1 | 11/1996 |
| WO | 1996034560 A1 | 11/1996 |
| WO | 1996034567 A1 | 11/1996 |
| WO | 1996034569 A1 | 11/1996 |
| WO | 1996034570 A1 | 11/1996 |
| WO | 1996034650 A1 | 11/1996 |
| WO | 1996034652 A1 | 11/1996 |
| WO | 1996034653 A1 | 11/1996 |
| WO | 1996036860 A2 | 11/1996 |
| WO | 1996039967 A1 | 12/1996 |
| WO | 1997015919 A1 | 5/1997 |
| WO | 1997017893 A1 | 5/1997 |
| WO | 1997017904 A1 | 5/1997 |
| WO | 1997025917 A1 | 7/1997 |
| WO | 1997025919 A1 | 7/1997 |
| WO | 1997032525 A1 | 9/1997 |
| WO | 1997036541 A1 | 10/1997 |
| WO | 1997040760 A1 | 11/1997 |
| WO | 1997042996 A1 | 11/1997 |
| WO | 1998018520 A2 | 5/1998 |
| WO | 1998019611 A1 | 5/1998 |
| WO | 1998026724 A1 | 6/1998 |
| WO | 1998028039 A1 | 7/1998 |
| WO | 1998038913 A1 | 9/1998 |
| WO | 1999002096 A1 | 1/1999 |
| WO | 1999056644 A1 | 11/1999 |
| WO | 1999056647 A1 | 11/1999 |
| WO | 1999056648 A1 | 11/1999 |
| WO | 1999056649 A1 | 11/1999 |
| WO | 2000078239 A2 | 12/2000 |
| WO | 2003041602 A2 | 5/2002 |
| WO | 2002060523 A2 | 8/2002 |
| WO | 2003089997 A2 | 10/2003 |
| WO | 2005027765 A1 | 3/2005 |
| WO | 2005027766 A1 | 3/2005 |
| WO | 2005065562 A1 | 7/2005 |
| WO | 2005065563 A1 | 7/2005 |
| WO | 2005104972 A2 | 11/2005 |
| WO | 2006017517 A2 | 2/2006 |
| WO | 2006044794 A2 | 4/2006 |
| WO | 2006049970 A2 | 5/2006 |
| WO | 2006052651 A1 | 5/2006 |
| WO | 2006052905 A2 | 5/2006 |
| WO | 2006055654 A1 | 5/2006 |
| WO | 2006055658 A1 | 5/2006 |
| WO | 2006055733 A1 | 5/2006 |
| WO | 2006055741 A1 | 5/2006 |
| WO | 2007016123 A2 | 2/2007 |
| WO | 2007024785 A2 | 3/2007 |

OTHER PUBLICATIONS

Oral et al., "Segmental ostial ablation to isolate the pulmonary veins during atrial fibrillation: feasibility and mechanistic insights," Circulation, vol. 106, pp. 1256-1262, 2002.

Nademanee et al., "A new approach for catheter ablation and atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

Oral et al.; U.S. Appl. No. 11/932,378 entitled "Ablation catheters and methods for their use," filed Oct. 31, 2007.

Werneth et al.; U.S. Appl. No. 12/116,753 entitled "Ablation therapy system and method for treating continuous atrial fibrillation," filed May 7, 2008.

Oral et al.; U.S. Appl. No. 12/176,115 entitled Atrial ablation catheter adapted for treatment of septal wall arrythmogenic foci and method of use.

\* cited by examiner

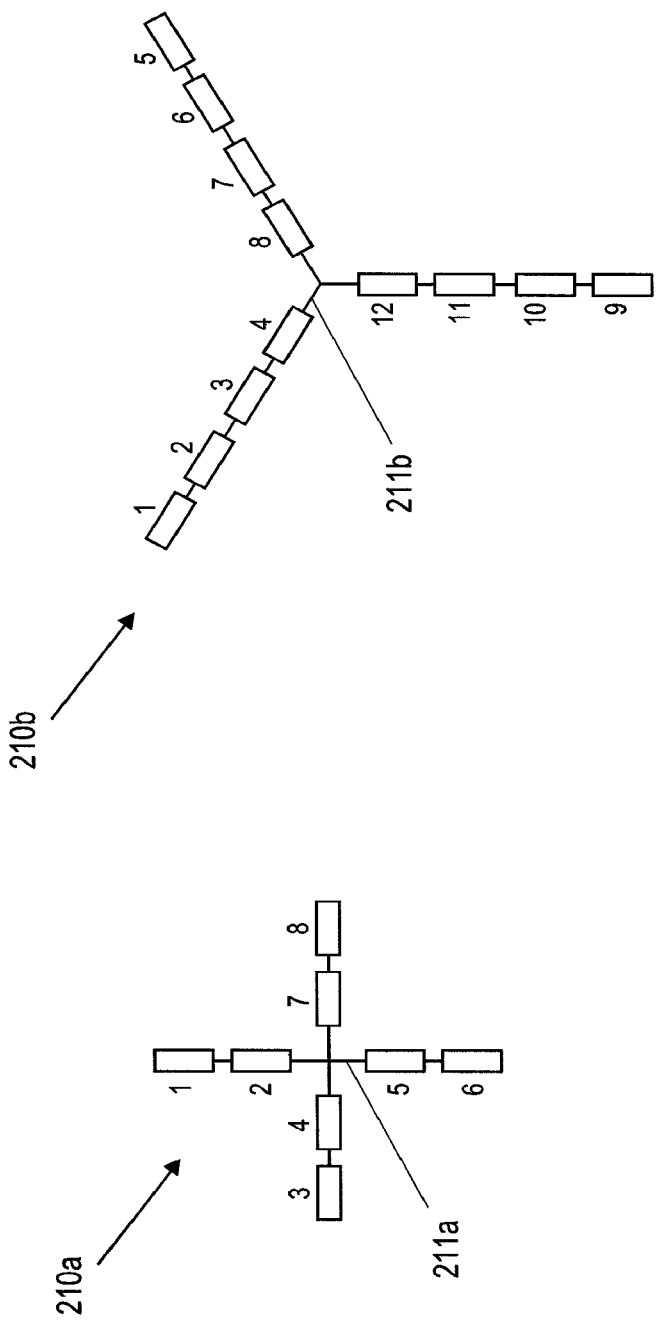

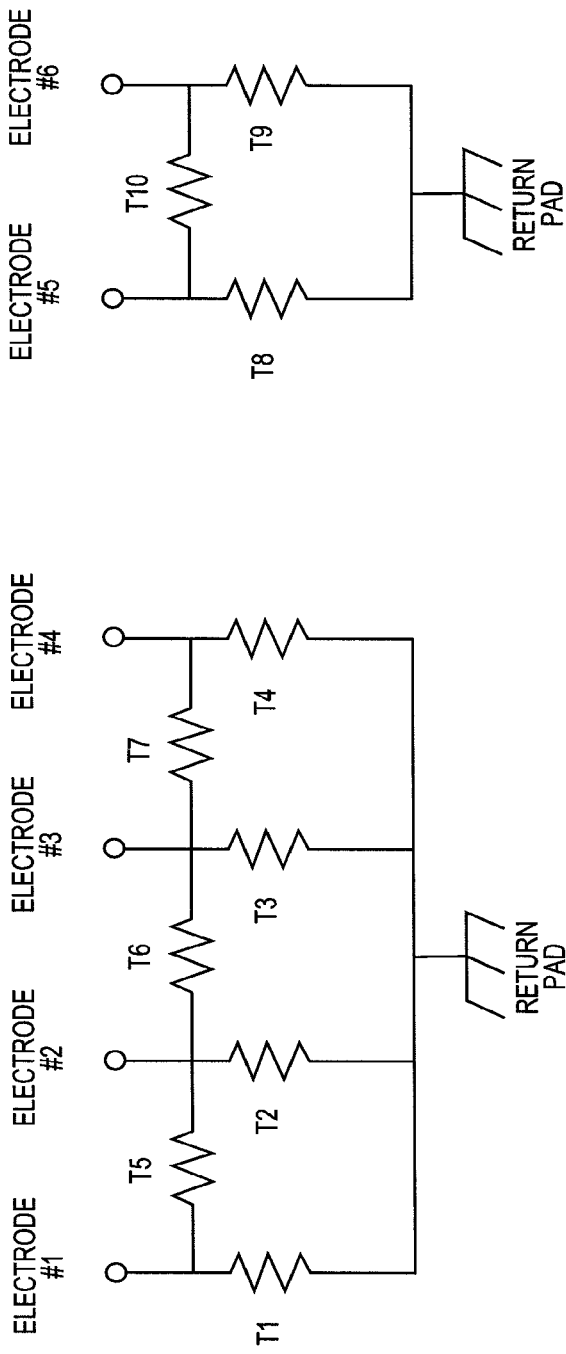

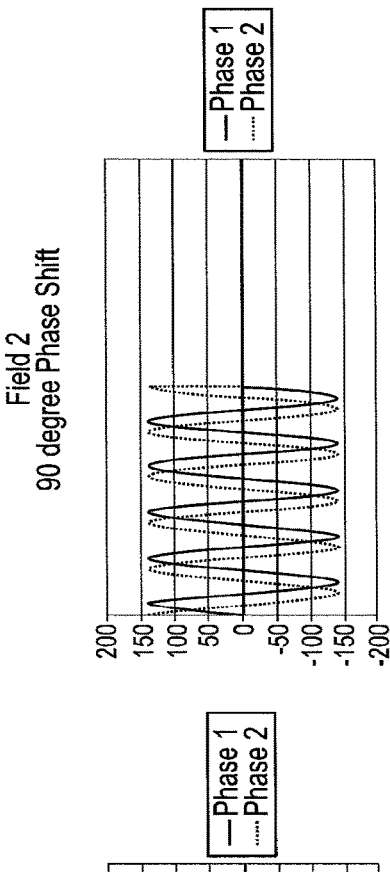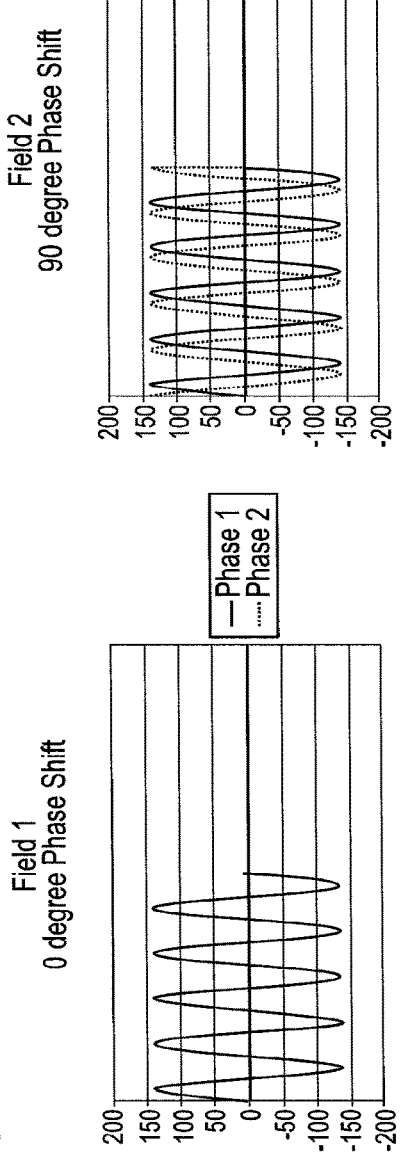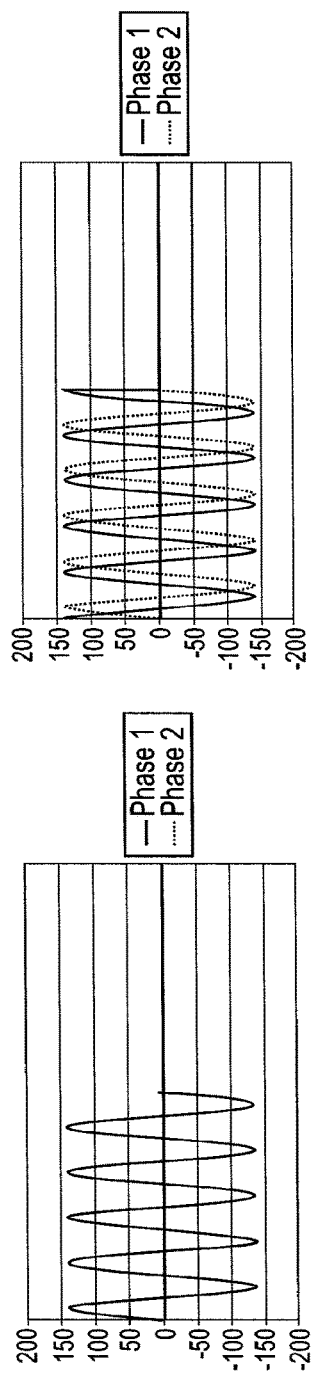
FIG. 9A  FIG. 9B  FIG. 9C  FIG. 9D

1:1
Bipolar/Unipolar Ratio

2:1
Bipolar/Unipolar Ratio

4:1
Bipolar/Unipolar Ratio

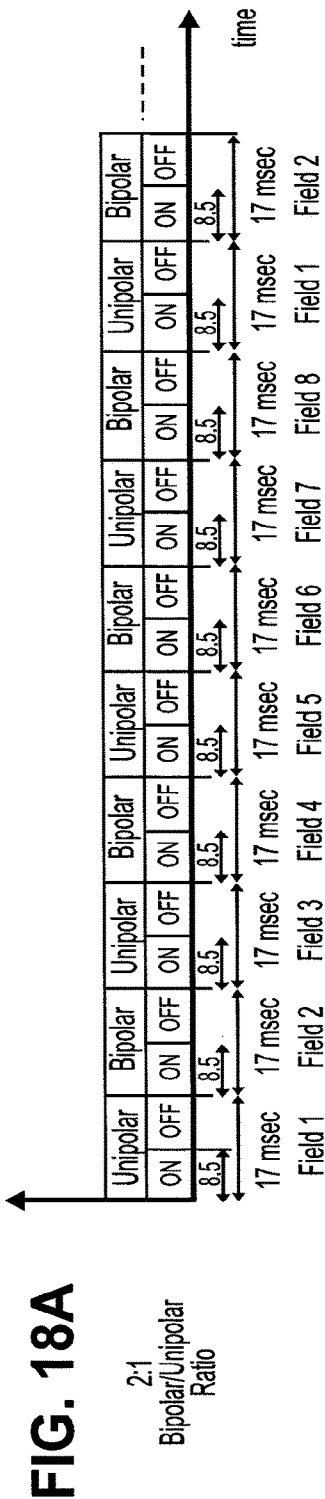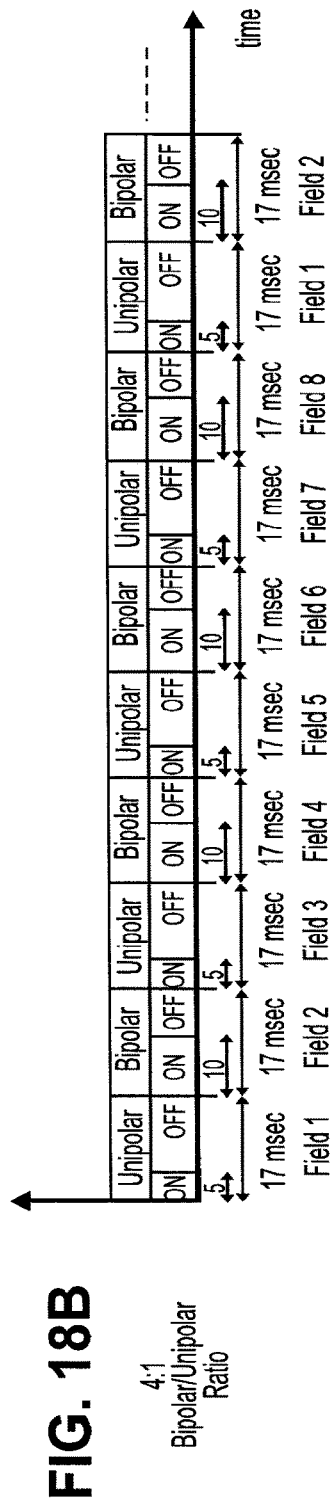
FIG. 18A
2:1 Bipolar/Unipolar Ratio
FIG. 18B
4:1 Bipolar/Unipolar Ratio

RF ENERGY DELIVERY SYSTEM

CROSS-REFERENCE TO RELATED APPLICATION

This application is a divisional of patent application Ser. No. 12/117,596, filed May 8, 2008, entitled RF ENERGY DELIVERY SYSTEM AND METHOD, issued on Jul. 8, 2014, as U.S. Pat. No. 8,771,269, the entirety of which is incorporated herein by reference.

STATEMENT REGARDING FEDERALLY SPONSORED RESEARCH OR DEVELOPMENT n/a

FIELD OF THE INVENTION

The present invention relates generally to ablation systems and methods for performing targeted tissue ablation in a patient.

BACKGROUND OF THE INVENTION

The present invention relates generally to ablation systems and methods for performing targeted tissue ablation in a patient. In particular, the present invention provides radiofrequency (RF) energy generators that create safe, precision lesions in tissue such as cardiac tissue.

Tissue ablation is used in numerous medical procedures to treat a patient. Ablation can be performed to remove or denature undesired tissue such as cancer cells. Ablation procedures may also involve the modification of the tissue without removal, such as to stop electrical propagation through the tissue in patients with an arrhythmia condition. Often the ablation is performed by passing energy, such as electrical energy, through one or more electrodes and causing the tissue in contact with the electrodes to heat up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. Atrial fibrillation affects 7% of the population over age 65

Atrial fibrillation treatment options are limited. Lifestyle change only assists individuals with lifestyle related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure and linear ablation procedures are tedious and time-consuming, taking several hours to accomplish. Pulmonary vein ostial ablation is proving to be difficult to do, and has lead to rapid stenosis and potential occlusion of the pulmonary veins. All ablation procedures involve the risk of inadvertently damaging untargeted tissue, such as the esophagus while ablating tissue in the left atrium of the heart. There is therefore a need for improved atrial ablation products and techniques that create efficacious lesions in a safe manner.

SUMMARY OF THE INVENTION

Several unique radiofrequency (RF) energy generators and ablation catheter systems and methods are provided which map and ablate large surface areas within the heart chambers of a patient, with one or few catheter placements. Any electrocardiogram signal site (e.g. a site with aberrant signals) or combination of multiple sites that are discovered with this placement may be ablated. In alternative embodiments, the RF generators and/or ablation catheters may be used to treat non-cardiac patient tissue, such as tumor tissue.

Advantages of the invention may include one or more of the following. The system and method provide maximum flexibility, efficacy and safety. The system and method provide independent delivery of monopolar and/or bipolar RF energy to multiple (e.g. 4, 8 or 12) user selectable electrodes. Monopolar energy delivery provides lesion depth and bipolar energy delivery provides lesion fill between selected electrodes. Sequential and/or simultaneous delivery of monopolar and bipolar RF energy can provide variable-depth linear lesions with a single or a reduced number of applications of energy. The system and method provide safe, precisely controlled delivery of RF energy to tissue.

In one embodiment, a constant voltage source is utilized for all pairs of RF outputs (channels) and adjustment of the phase angle of the applied (RF) voltage produces different ratios of simultaneous and/or cumulative monopolar and bipolar energy delivered such as to create varied length and depth lesions in the tissue of a patient.

In another embodiment, a varied voltage source is utilized for all pairs of RF outputs and adjustment of the voltage amplitude or other applied voltage property produces different ratios of simultaneous and/or cumulative monopolar and bipolar energy delivered such as to create varied length and depth lesions in the tissue of a patient. In this embodiment, the duty cycle used during energy delivery may be fixed, or alternatively it may be varied such as a configuration in which a minimal duty cycle is used which incrementally increases to reach a target tissue temperature. In this embodiment, the phase shift may be fixed, such as fixed at 90° or 180° phase shift to create the bipolar energy. The RF generator of this embodiment includes variable power supply circuits for each RF output.

In yet another embodiment, varying the average "on" time of bipolar and/or monopolar power delivery is utilized for all pairs of RF outputs and adjustment of this average produces different ratios of simultaneous and/or cumulative monopolar and bipolar energy delivered such as to create varied length and depth lesions in the tissue of a patient. The ratio of bipolar fields (or combined monopolar-bipolar fields) to monopolar fields may be adjusted to achieve a desired power level and/or bipolar-monopolar ratio. Alternatively or additionally, the duty cycle ratio within the bipolar fields (or combined monopolar-bipolar fields) and the monopolar fields may be adjusted to achieve the desired power level and/or bipolar-monopolar ratio. Alternatively or additionally, the fields length of the bipolar fields (or combined monopolar-bipolar fields) and the monopolar fields may be adjusted to achieve the desired power level and/or bipolar-monopolar ratio.

The RF generators of the present invention may employ one or more energy delivery algorithms to control power delivery. In one embodiment, an algorithm provides energy at a fixed power, such as a maximum power, until the tissue to be ablated reaches a first temperature level. For temperatures above the first temperature level, power is delivered at a level determined by the actual tissue temperature. Target temperature levels and/or threshold temperatures may be adjustable by an operator of the system. In another embodiment, an algorithm employs a main control loop based on a power differential analysis and a secondary control loop based on a temperature differential analysis.

The RF generators of the present invention may employ a multiplexing module which allows an operator of the system to selectively pair RF outputs from a group of three or more RF outputs to deliver bipolar energy between the selected pair.

In another embodiment, the system and method include closed loop energy delivery for each RF output including a PID control loop which receives information from a thermocouple mounted proximate each electrode on the ablation catheter such as to provide closed loop energy delivery based on measured tissue temperature. Power delivery may be duty cycle controlled to improve lesion creation efficiency, providing low power ablations. Duty cycle control allows delivery of high peak powers while providing electrode cooling times during the off cycle. In addition, duty cycle power control simplifies design and control of multiple RF outputs utilizing different phase angles. Duty cycle energy delivery also improves temperature acquisition as data can be acquired during the off portion of the duty cycle (i.e., during the RF "quiet time"). The system and method including temperature acquisition provide fast, accurate and electrically-isolated temperature acquisition for all electrodes. Each catheter electrode may include a small mass thermocouple. The system and method provide safe, controlled energy delivery.

In yet another embodiment, the RF generator includes a first set of ablation parameters that are utilized when a first form of ablation catheter is attached to the RF outputs and a second set of ablation parameters that are utilized when a second form of ablation catheter is attached to the RF outputs.

In yet another embodiment, the RF generator includes an improved EKG interface for connecting the RF outputs to an EKG diagnostic device. When one or more ablation catheters are attached to the RF generator, the electrodes of the ablation catheter are electrically attached to the RF outputs of the RF generator. The improved EKG interface of the present invention attenuates the energy delivered to ablate tissue to a level to prevent damage to any attached EKG diagnostic device, yet allows EKG or other signals sensed by the electrodes to be transferred to the EKG diagnostic device with minimal attenuation of those signals.

According to another aspect of the invention, a system for performing an ablation procedure is described. In one embodiment, one or more ablation catheters are provided with an RF generator of the present invention. In another embodiment, a remote control is provided with the RF generator of the present invention.

One aspect of the invention provides a radio frequency tissue ablation system including a radio frequency generator. The generator has a radio frequency source, at least four independently controllable radio frequency outputs, a user interface and a controller configured to delivery radio frequency energy from the radio frequency source to the radio frequency outputs in one of at least two different output configurations in response to a configuration selection made through the user interface. In some embodiments, the controller is further configured to operate each output in either a monopolar mode or in a bipolar mode or possibly in a combination monopolar/bipolar mode, possibly in response to a configuration selection made through a user interface. The system may also include a ground pad connected to a ground source when the outputs are operated in both monopolar mode and bipolar mode.

In some embodiments, the controller is further configured to deliver radio frequency energy from the radio frequency source to the radio frequency outputs in a plurality of successive time fields each having a period. The time fields may have a duty cycle with a portion of the period when radio frequency energy is being delivered to the outputs and another portion of the period when radio frequency energy is not being delivered to the outputs. The controller may be further configured to adjust the duty cycle in response to a configuration selection made through the user interface. In some embodiments, at least one time field of the plurality of the successive time fields is monopolar for at least a portion of the period, and at least another time field of the successive time fields is bipolar for at least a portion of the period. In such embodiments, the controller may be configured to adjust a ratio of bipolar to monopolar time fields in response to a configuration selection made through the user interface. One time field may be a combination monopolar/bipolar time field. The controller may also be further configured to adjust a length of at least one time field in response to a configuration selection made through the user interface.

In some embodiments, the radio frequency source is a constant voltage source, and in some embodiments the radio frequency source is a variable voltage source, in which case the controller may be further configured to vary voltage amplitude in response to a configuration selection made through the user interface. In some embodiments the controller is further configured to adjust voltage phase angle of the RF source, possibly in response to a configuration selection made through the user interface. In some embodiments, the controller includes a time division multiplexor.

In some embodiments, the radio frequency generator further includes an electrode tool interface configured to detect an identifier of a radio frequency electrode tool connected to the interface, the controller being configured to adjust radio frequency energy delivery parameters to an radio frequency electrode tool based on the identifier detected by the interface. Such systems may also include a first radio frequency electrode tool having a first electrode configuration and second radio frequency electrode tool having a second electrode configuration different from the first electrode configuration, the first and second radio frequency electrode tools each having a connector adapted to connect to the radio frequency generator electrode tool interface, the connector of each tool having a unique identifier adapted to communicate with the radio frequency generator electrode tool interface.

Some embodiments according to this aspect of the invention have a ground pad, with the controller being configured to connect and disconnect the ground pad to a ground source in response to a configuration selection made through the user interface. In some embodiments, each output has an output line, a return line and a resistance between output line and the return line. The resistance may have a value that provides signal stability on the output during light load conditions at the output.

Another aspect of the invention provides a radio frequency ablation system having a radio frequency generator; a plurality of radio frequency electrodes; a temperature sensor; and a controller communicating with the temperature sensor to control an amount of energy delivered to the electrodes in a first portion of an energy delivery session irrespective of temperature sensed by the temperature sensor and in a second portion of the energy delivery session based on the temperature sensed by the temperature sensor. In some embodiments, the controller is configured to cease energy delivery to the electrodes when a predetermined target temperature is sensed by the temperature sensor. The system may also have a user interface adapted to set the target temperature.

In some embodiments, the controller is further configured to cease the first portion of the energy delivery session when the temperature sensor reaches a threshold temperature that is a predetermined amount lower than the target temperature. In some embodiments, the controller is configured to cease the first portion of the energy delivery session when temperature sensed by the temperature sensor reaches a threshold temperature. The system may also have a user interface adapted to set the threshold temperature.

In some embodiments, the controller is configured to independently control energy delivery to each electrode. The system may also have a temperature sensor associated with each electrode, with the controller independently communicating with each temperature sensor in the delivering step to control the amount of energy delivered to the electrodes. In some embodiments, the controller is configured to independently control energy to a pair of electrodes and at least one other electrode.

In some embodiments, the controller is configured to deliver radio frequency energy in a plurality of successive time fields each having a period and a duty cycle comprising a portion of the period when radio frequency energy is being delivered to the electrodes and another portion of the period when radio frequency energy is not being delivered to the electrodes. The controller may also be further configured to adjust the duty cycle based on monitored temperature.

Yet another aspect of the invention provides a radio frequency energy generation system for delivering radio frequency energy to a cardiac ablation catheter. In some embodiments, the system has a radio frequency generator adapted to deliver radio frequency energy in both monopolar and bipolar modes to an ablation catheter, wherein the ablation catheter has an electrode array comprising at least one electrode; an EKG monitoring unit adapted to monitor and map signals detected by the plurality of ablation catheters; and an interface unit including an inductor which couples the radio frequency generator and EKG monitoring unit to filter radio frequency signals from EKG signals received by the EKG monitoring unit.

In some embodiments, the at least one electrode is adapted to monitor the temperature of atrial tissue adjacent the electrode, and the generator generates radio frequency energy based on the temperature of the atrial tissue. There may be a plurality of electrodes, and the generator may be adapted to independently monitor the temperature of atrial tissue measured by each of the plurality of electrodes, and the radio frequency generator may be adapted to generate and deliver radio frequency energy to each of the plurality of electrodes based on the independently monitored temperatures.

In some embodiments, the EKG monitoring unit has a plurality of inputs and an inductor associated with each input. In some embodiments, the generator is adapted to deliver energy in a bipolar mode, a monopolar mode, and a combination of both bipolar and monopolar, such as in bipolar to monopolar ratios of at least 4:1, 2:1, and 1:1.

Still another aspect of the invention provides a method of delivering radio frequency ablation energy to a patient's tissue, such as heart tissue, prostate tissue, brain tissue, gall bladder tissue, uterine tissue, or tumor tissue. The method includes the steps of delivering radio frequency energy to a plurality of electrodes to heat the patient's tissue in first and second portions of an energy delivery session; monitoring temperature of the patient's tissue during the delivering step; delivering radio frequency energy at a power level in the first portion of the energy delivery session, the power level being irrespective of monitored tissue temperature; and controlling radio frequency energy delivered to the electrodes in the second portion of the energy delivery session based on monitored tissue temperature.

In some embodiments, the method includes the step of ceasing energy delivery when a predetermined target tissue temperature is reached. The method may also include the step of setting the target tissue temperature. In some embodiments, the method includes the step of ceasing the first portion of the energy delivery session when monitored tissue temperature reaches a threshold tissue temperature that is a predetermined amount lower than the target tissue temperature.

In some embodiments, the first portion of the energy delivery session ceases when a threshold tissue temperature is reached. The method may also include the step of setting the threshold tissue temperature. In some embodiments, at least one of the controlling steps includes the step of independently controlling energy delivery to each electrode or to a pair of electrodes and to at least one other electrode.

In some embodiments, the delivering step includes the step of delivering radio frequency energy in a plurality of successive time fields each having a period and a duty cycle, where the duty cycle has a portion of the period when radio frequency energy is being delivered to the electrodes and another portion of the period when radio frequency energy is not being delivered to the electrodes. In some embodiments, at least one of the controlling steps includes the step of adjusting the duty cycle.

In some embodiments, the step of controlling radio frequency energy delivered to the electrodes in the second portion of the energy delivery session includes the step of comparing a monitored temperature to a target temperature and adjusting a power goal. The delivering step may also include the step of comparing the power goal to a power limit and resetting the power goal to the power limit if the power goal exceeds the power limit.

In various embodiments of the invention, a radiofrequency generator for delivering energy to ablate tissue of a patient has at least four, at least eight, at least twelve or at least sixteen independent RF outputs configured to provide energy to four or more electrodes of an ablation catheter. In various embodiments of the generator, independent RF outputs can deliver at least monopolar, bipolar, and combination bipolar/monopolar energy.

Another embodiment of the invention is a radiofrequency generator for delivering energy to ablate tissue of a patient having a power scheme, including an algorithm, which initially delivers energy to a maximum power level until the tissue reaches a first temperature, and subsequently delivers temperature regulated power until the tissue reaches a second temperature.

Another embodiment of the invention is a radiofrequency generator for delivering energy to ablate tissue of a patient; the invention having a power scheme, including an algorithm, which delivers bipolar and monopolar and combination power to multiple RF outputs and which adjusts the bipolar to monopolar ratio by varying phase angle.

Another embodiment of the invention is a radiofrequency generator for delivering energy to ablate tissue of a patient having a power scheme, including an algorithm, which delivers bipolar and monopolar and combination power to multiple RF outputs and which adjusts the bipolar to monopolar ratio by varying the voltage source.

Another embodiment of the invention is a radiofrequency generator for delivering energy to ablate tissue of a patient has a power scheme, including an algorithm, which delivers bipolar and monopolar and combination power to multiple RF outputs and which delivers the bipolar and monopolar power in sets of multiple repeating fields and adjusts the bipolar to monopolar ratio by varying the average "on" time of the bipolar and/or monopolar power delivery within each of said sets of multiple repeating fields.

Another embodiment of the invention is a radiofrequency generator, for delivering energy to ablate tissue of a patient, having a power scheme, including an algorithm, which delivers power to multiple RF outputs with a first duty cycle percentage, and increases the duty cycle percentage to achieve a target temperature such as to maximize the off-time portion of the duty cycle.

Another embodiment of the invention is a radiofrequency generator, for delivering energy to ablate tissue of a patient, having multiple RF outputs which are configured to be selectively paired to deliver bipolar energy between the selected pair.

Another embodiment is a radiofrequency generator, for delivering energy to ablate tissue of a patient, having at least four independent temperature inputs which are configured to receive temperature information and produce four corresponding temperature signals, and at least four PID loops configured to receive the four temperature signals and regulate RF power delivery.

Another embodiment is a radiofrequency generator for delivering energy to ablate tissue of a patient, having a first set of ablation parameters configured to be utilized when a first ablation catheter is attached, and a second set of ablation parameters configured to be utilized when a second ablation catheter is attached.

Another embodiment is a radiofrequency generator for delivering energy to ablate tissue of a patient, having an EKG interface module configured to isolate an EKG monitoring unit from delivered RF energy while minimizing attenuation of EKG signals received from the electrodes of the ablation catheter.

In further embodiments of the invention, the power scheme may initially deliver energy at a maximum power level until the tissue reaches a first temperature and subsequently delivers temperature regulated power until the tissue reaches a second temperature. The first temperature may be set by an operator of the system, or may be automatically set to a temperature approximately 5° less than the second temperature. In another embodiment, the second temperature of the radiofrequency generator is set by an operator of the system. In another embodiment, both the first and second temperatures are set by an operator of the system. In yet another embodiment, the first temperature is automatically set to a temperature approximately 5° less than the second temperature.

In another embodiment, the voltage source is varied by varying the RMS voltage, and more particularly by varying the peak amplitude.

In other embodiments, the power scheme of the generator may also include an algorithm that delivers bipolar and monopolar power to multiple RF outlets, and adjusts the bipolar to monopolar ratio by varying one or more of the phase angle, voltage source, the RMS voltage and the peak amplitude. In still other embodiments, the power from the generator is delivered in multiple fields, and each field has a set duty cycle percentage. The duty cycle may be set between about 5 and about 25%. In some embodiments, the generator may have a least four, or at least 12, variable power supply circuits. In some embodiments, the power from the generator may be delivered in multiple fields, each field having an initial duty cycle percentage, said duty cycle percentage increasing to achieve a target temperature.

In alternate embodiments, the radiofrequency generator has at least four, or at least twelve variable power supply circuits.

In some embodiments, the algorithm of the power scheme delivers bipolar and/or monopolar power in sets of multiple repeating fields and the generator is adjusted by adjusting the ratio of monopolar fields to combination fields and/or bipolar fields by varying the average "on" time of the bipolar and/or monopolar power delivery within each of said sets of multiple repeating fields. The average "on" time may be adjusted by adjusting one or more of the ratio of monopolar to combination and/or bipolar fields with a set, the duty cycle ratio within one or more fields in the set, and the field length of one or more fields within the set. The RF outputs of the generator may be in-phase or out-of-phase and the systems include a ground pad that is always electrically connected. Out-of-phase energy delivery may be accomplished with a 90° or 180° phase shift.

In some embodiments, the algorithm of the power scheme may deliver power to multiple RF outputs with a first duty cycle percentage and increase the duty cycle percentage to achieve a target temperature such as to maximize the off-time portion of the duty cycle.

In some embodiments, the generator may have multiple RF outputs which are configured to be selectively paired to deliver bipolar energy between the selected pair.

In some embodiments, the generator may have at least four independent temperature inputs configured to receive temperature information and produce at least four corresponding temperature signals, and at least four PID loops configured to receive the at least four temperature signals and regulate RF power delivery.

In some embodiments, the generator may have a first set of ablation parameters configured to be utilized when a first ablation catheter is attached, and a second set of ablation parameters configured to be utilized when a second ablation catheter is attached. The power delivered is dependent on one or more parameters of the ablation catheter receiving ablation energy, said parameters selected from the group consisting of distance between two electrodes, electrode geometry, thermocouple location and combinations thereof.

In some embodiments, the RF generator may have an EKG interface module configured to isolate an EKG monitoring unit from delivered RF energy while minimizing attenuation of EKG signals received from the electrodes of the ablation catheter. The EKG interface module may include an inductor to attenuate the RF energy, which may have approximately 1000 milliHenry of inductance.

In some embodiments, the RF generator may deliver energy in monopolar or combination mode only such that the return pad remains electrically connected during energy delivery. In certain embodiments, the bipolar portion may be created with 90° or 180° phase shifted applied voltages.

In some embodiments, the generator may have a signal generator for each two RF outputs. The first signal generator may be synchronized in time with a second signal generator. Each signal generator may be under microprocessor control.

In some embodiments, the power from the generator may be duty cycle controlled, and may be adjusted in a series of discrete steps, which may be at least 256 steps. The duty cycle period may be a period of time less than the thermal time constant of the tissue to be ablated. The duty cycle period may be approximately 17 milliseconds or between 10 and 500 milliseconds and may be configured to be adjusted by an operator. In another embodiment, the duty cycle may be approximately 10%, and may be between about 5% and about 25%.

In some embodiments, the bipolar power delivered by the generator may be created by a phase shift between applied voltages, said phase shift adjustable in discrete steps, such as 16 steps. The applied voltage may be between about 20 and 200 volts RMS, more specifically 40 volts RMS, or 100 volts RMS. In some embodiments the applied voltage has a frequency of approximately 470 KHz.

In some embodiments, power delivered by the generator maybe adjustable by an operator. In some embodiments the delivered power may be adjustable between 0 and 80 watts RMS. The delivered power may be adjusted by varying phase shift; duty cycle percentage; duty cycle period; applied voltage; frequency of applied voltage; shape of applied voltage such as sinusoidal, triangular wave, or square wave shapes; connections to the return pad; voltage applied to return pad; and combinations thereof. The bipolar to monopolar ratio may be adjusted. The delivered power may be adjusted by microprocessor control. In other embodiments, the power delivered by the generator is adjusted by microprocessor control.

In some embodiments, the generator may deliver power during a set of repeating fields, said fields including an "on" time and an "off." The set of repeating fields may include 4 or 8 fields. Each field may have a period between about 10 and 500 milliseconds, more specifically approximately 17 milliseconds. The generator may deliver power during the "on" time including at least one of monopolar power, bipolar power, and combination power. The power delivered during the "on" time may be limited to monopolar or combination power.

In some embodiments, the generator may have an algorithm that includes at least one power limit. The power limits may include multiple power limits. The first power limit may be applicable to a first ablation catheter and a second power limit applicable to a second ablation catheter. In another embodiment, the first power limit may be applicable to a first bipolar-monopolar ratio and a second power limit applicable to a second bipolar-monopolar ratio. The power limit for the greater bipolar-monopolar ratio may be less than the power limit for the lesser bipolar-monopolar ratio. The power limit may be approximately 10 watts RMS and applicable to a monopolar-only power delivery. The power limit of approximately 10 watts RMS may be applicable to a monopolar-bipolar ratio of 1:1, 2:1, or 4:1. The power limit of approximately 6 watts RMS may be applicable to a bipolar-only power delivery. A power limit of approximately 20 watts may be applicable to at least one electrode of an ablation catheter. A power limit of approximately 30 watts may be applicable to at least one electrode of an ablation catheter.

In some embodiments, the generator may have a return pad that is electrically connected to a return or common connection of all the RF outputs. The return pad may be electrically connected during all energy deliveries.

In some embodiments, the generator may provide duty cycle controlled energy delivery and one or more measurements are performed during the "off" time of a duty cycle. The measurement may be an analysis of information received from a temperature sensor. The temperature sensor may be a thermocouple of an ablation catheter. The measurement may be an analysis of information received from an EKG sensor. The EKG sensor may be an electrode of an ablation catheter.

In some embodiments, the generator may be configured to provide electrical isolation between at least one component of the generator and the patient. The electrical isolation provided may be at least 5000 volts of electrical isolation. The at least one component may be an RF output of the generator. The generator may have a temperature input configured to receive temperature information from a thermocouple, and said at least one component is said temperature input.

In some embodiments, the generator may have a temperature sensor module configured to receive temperature information from multiple temperature sensors. The temperature sensor module may include at least 4, at least 8, or at least 12 independent channels. The temperature sensor module may include multiple independent control loops configured to provide feedback to regulate power based on current temperature information received from the temperature sensors and target temperature information set by an operator of the system. In some embodiments, the target temperature information may be selected from the range of 50° C. to 70° C. In some embodiments, the generator my have a second target temperature, said second target temperature used in combination with the first target temperature by a power control algorithm of the generator. In some embodiments, the temperature sensor module may include an amplifier for each temperature input, each amplified configured to amplify the signal. The amplifier may have a gain of approximately 100. In some embodiments, the temperature ratio between the various electrodes may be controlled by adjusting each RF output's duty cycle, such as to balance the temperature across the lesion.

In some embodiments, the generator may have bipolar to monopolar power delivery controlled using time division multiplexing.

In some embodiments, the generator is configured is configured to perform cardiac procedures selected from the group consisting of atrial fibrillation procedures; supra ventricular tachycardia procedures; atrial tachycardia procedures; supra ventricular tachycardia procedures; ventricular fibrillation procedures; and combinations thereof.

In some embodiments, the generator is configured to perform tumor ablation procedures.

In some embodiments, the generator is configured to perform procedures selected from the group consisting of: prostate procedures; brain procedures; gall bladder procedures; uterus procedures; and combinations thereof.

In some embodiments, the generator further has at least one ablation catheter. In some embodiments, the ablation catheter is configured to perform a pulmonary vein ablation procedure. The ablation catheter may include at least one electrode with a mass between 30 and 50 milligrams, more specifically approximately 40 milligrams. The ablation catheter may have at least one thermocouple with a mass between 48 and 88 micrograms, more specifically approximately 68 milligrams. The ablation catheter may include at least one thermocouple constructed of wire of approximately 38 gauge. The ablation catheter may be configured to perform an atrial wall ablation procedure. The ablation catheter may include at least one electrode with a mass between 17 and 37 milligrams, more specifically approximately 27 milligrams. The ablation catheter may include at least one thermocouple with a mass between 22 and 62 micrograms, more specifically 43 micrograms. The ablation catheter may include at least one thermocouple constructed of wire of approximately 40 gauge. The ablation catheter may include at least one electrode with a wall thickness between 0.004" and 0.010", more specifically approximately 0.006". The ablation catheter may include at least one electrode including a heat sink. The at least one electrode including a heat sink may be a projecting fin.

In some embodiments the generator may include a static load electrically connected to each RF amplifier configured to stabilize the RF output. The static load may be approximately 2000 ohms of impedance.

In some embodiments, the generator may include an algorithm which requires a minimum ablation energy delivery time. The minimum ablation energy delivery time may be 25, or 40 seconds.

Another embodiment of the invention is a system for delivering energy to ablate tissue of a patient, having a remote controller for the radiofrequency generator and having a radiofrequency generator. The controller has a user interface configured to allow an operator to send commands to the radiofrequency generator or to provide to an operator information received from the radiofrequency generator. The remote controller may both send commands and provide information to an operator, and the commands and/or said information may be transferred over a wired or wireless connection. The remote controller may be sterile, and may be a sterile bag configured to surround at least the housing of the remote controller. The user interface may provide the same set of commands, or may provide the same set of information, as the user interface of the RF generator.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIGS. 6A and 6B illustrate end views of electrode carrier assemblies of two different ablation catheters, consistent with the present invention.

FIGS. 7A and 7B each illustrate a circuit equivalent to electrode-tissue interaction employed to demonstrate generation of bipolar and/or monopolar currents, consistent with the present invention.

FIG. 9A-D illustrate a power delivery scheme including four fields configured to deliver a 1:1 ratio of bipolar to monopolar power, consistent with the present invention.

FIGS. 18A and 18B illustrates power delivery schemes in which the bipolar to monopolar ratio is set by varying the duty cycle percentage within the bipolar and/or monopolar fields, consistent with the present invention.

DETAILED DESCRIPTION OF THE INVENTION

Figure 1:
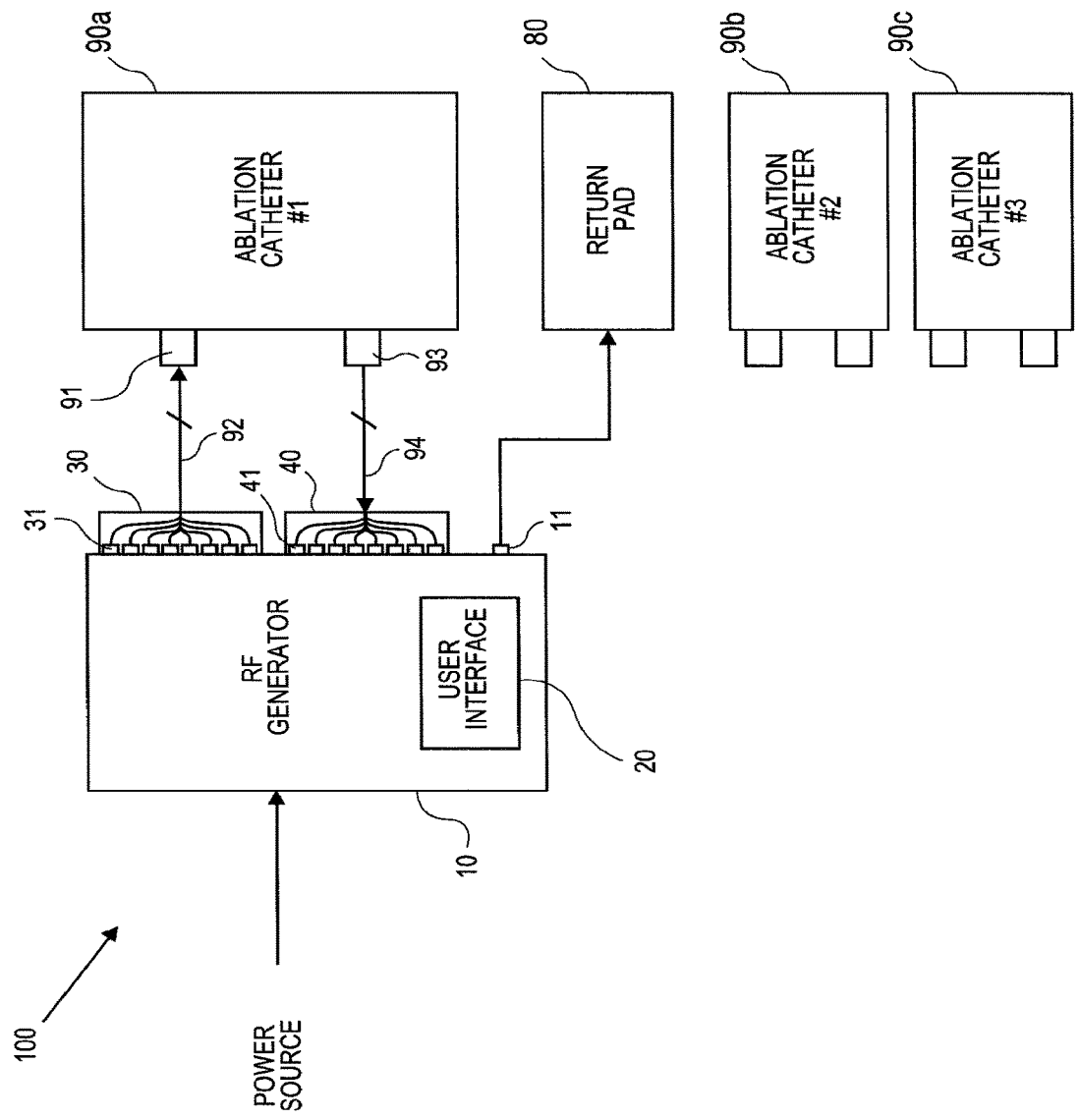
FIG. 1 illustrates a schematic depiction of an RF generator, consistent with the present invention.

Reference will now be made in detail to the present embodiments of the invention, examples of which are illustrated in the accompanying drawings. Wherever possible, the same reference numbers will be used throughout the drawings to refer to the same or like parts The present invention provides catheters for performing targeted tissue ablation in a subject. In some embodiments, the catheters comprise a tubular body member having a proximal end and distal end and a lumen extending therebetween. The catheter is of the type used for performing intracardiac procedures, typically being introduced from the femoral vein in a patient's leg or from a vessel in the patient's neck. The catheter is introducible through a sheath and also has a steerable tip that allows positioning of the distal portion such as when the distal end of the catheter is within a heart chamber. The catheters include ablation elements mounted on a carrier assembly. The carrier assembly is attached to a coupler, which in turn is connected to a control shaft that is coaxially disposed and slidingly received within the lumen of the tubular body member. The carrier assembly is deployable by activating one or more controls on a handle of the catheter, such as to engage one or more ablation elements against cardiac tissue, typically atrial wall tissue or other endocardial tissue.

Arrays of ablation elements, such as electrode arrays, may be configured in a wide variety of ways and patterns. In particular, the present invention provides devices with electrode arrays that provide electrical energy, such as radiofrequency (RF) energy, in monopolar mode, bipolar mode or combined monopolar-bipolar mode, as well as methods for treating conditions (e.g., atrial fibrillation, supra ventricular tachycardia, atrial tachycardia, ventricular tachycardia, ventricular fibrillation, and the like) with these devices.

The normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters and RF generators of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element is next placed near the targeted cardiac tissue that is to be ablated. The physician directs energy, provided by a source external to the patient, from one ore more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the focus of the disorder. For treatment of atrial fibrillation, currently available methods and devices have shown only limited success and/or employ devices that are extremely difficult to use or otherwise impractical.

The ablation systems of the present invention allow the generation of lesions of appropriate size and shape to treat conditions involving disorganized electrical conduction (e.g., atrial fibrillation). The ablation systems of the present invention are also practical in terms of ease-of-use and limiting risk to the patient (such as in creating an efficacious lesion while minimizing damage to untargeted tissue), as well as significantly reducing procedure times. The present invention addresses this need with, for example, carrier assemblies with 3 or 4 carrier arms, carrier assemblies with forward facing electrodes, carrier assemblies with rear-facing electrodes and carrier assemblies configured in a helix or partial helix. The carrier assemblies include ablation elements such as electrodes which create spiral, radial, or other simple or complex shaped patterns of lesions in the endocardial surface of the atria by delivery of energy to tissue or other means. The electrodes may include projecting fins to improve cooling properties. The lesions created by the ablation catheters and RF generators of the present invention are suitable for inhibiting the propagation of inappropriate electrical impulses in the heart for prevention of reentrant arrhythmias, while minimizing damage to untargeted tissue, such as the esophagus or phrenic nerve of the patient.

Definitions

To facilitate an understanding of the invention, a number of terms are defined below.

As used herein, the terms "subject" and "patient" refer to any animal, such as a mammal like livestock, pets, or a human. Specific examples of "subjects" and "patients" include, but are not limited, to individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure an ablation catheter is inserted into the heart using fluoroscopy for visualization, and then an energy delivery apparatus is used to direct energy to the heart muscle via one or more ablation elements of the ablation catheter. This energy either "disconnects" or "isolates" the pathway of the abnormal rhythm (depending on the type of ablation). It can also be used to disconnect the conductive pathway between the upper chambers (atria) and the lower chambers (ventricles) of the heart. For individuals requiring heart surgery, ablation can be performed during coronary artery bypass or valve surgery.

As used herein, the term "ablation element" refers to an energy delivery element, such as an electrode for delivering electrical energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. In monopolar energy delivery mode, the energy is conducted from the electrode, through the tissue to a return or ground pad, such as a conductive pad attached to the back of the patient. The high concentration of energy at the electrode site causes localized tissue ablation. In bipolar energy delivery mode, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is one embodiment of this application.

As used herein, the term "carrier assembly" refers to a flexible carrier, on which one or more ablation elements are disposed. Carrier assemblies are not limited to any particular size, or shape, and can be configured to be constrained within an appropriately sized lumen.

As used herein, the term "carrier arm" refers to a wire-like shaft capable of interfacing with electrodes and the coupler. A carrier arm is not limited to any size or measurement. Examples include, but are not limited to: stainless steel shafts; Nitinol shafts; titanium shafts; polyurethane shafts; nylon shafts; and steel shafts. Carrier arms can be entirely flexible, or may include flexible and rigid segments.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "coagulum" refers to a blood mass or clot such as a clot which may be caused by excessive heating in blood.

As used herein, the terms "return pad" or "ground pad" interchangeably refer to a surface electrode mounted to the patient's body, typically on the patient's back. The return pad receives the RF ablation currents generated during monopolar power delivery. The return pad is sized (large enough) such that the high temperatures generated remain within a few millimeters of the specific ablation catheter's electrode delivering the monopolar power.

As used herein, the term "RF output" refers to an electrical output produced by the RF generator of the present invention. The RF output is electrically connected to a jack or other electro-mechanical connection means which allows electrical connection to one or more electrodes of an ablation catheter. The RF output provides the RF energy to the electrode to ablate tissue with bipolar and/or monopolar energy.

As used herein, the term "channel" refers to a pair of RF outputs between which bipolar energy is delivered. Each of the RF outputs in a channel may also deliver monopolar energy (simultaneous and/or sequential to bipolar energy delivery), such as when a return pad is connected.

As used herein, the term "targeted tissue" refers to tissue identified by the clinician (and/or one or more algorithms of the system) to be ablated, such as to disconnect an aberrant electrical pathway causing an arrhythmia, or other undesired tissue such as cancer tissue.

As used herein, the term "untargeted tissue" refers to tissue which is desired to avoid damage by ablation energy, such as the esophagus or phrenic nerve in an arrhythmia ablation procedure.

As used herein, the term "set ablation time" refers to a time period over which ablation energy is delivered to targeted tissue in a relatively continuous manner, to ablate that tissue. The set ablation time is set by the operator and/or automatically set by one or more algorithms of the system of the present invention.

As used herein, the term "duty cycle" refers to the proportion of time during which a component, device or system is operated. The duty cycle can be expressed as a ratio or as a percentage. A microwave oven is a good example of a product that uses duty cycle for power control. At, e.g., power level one, the oven will be on for one second, and then off for nine seconds. This cycle repeats until the timer runs out. The oven is on for one out of ten seconds, or $1/10$ of the time, and its duty cycle is therefore $1/10$ or 10 percent.

As used herein, the term "field" refers to a single period of a duty cycle. Each field includes an "on" time in which energy is delivered and an "off" time in which no energy is delivered. In the system of the present invention, a sequential set of fields (e.g. 2, 4, 8) have a customized power delivery scheme which repeats over time.

As used herein, the term "power delivery scheme" refers to a set of ablation parameters to be delivered during a set ablation time, and used to safely create an effective lesion in targeted tissue. Power delivery scheme parameters include but are not limited to: type (bipolar and/or monopolar) of energy delivered; voltage delivered; current delivered; frequency of energy delivery; duty cycle parameter such as duty cycle percentage or length of period; field parameter such as configuration of fields or number of fields in set that repeats; and combinations thereof.

As used herein, the term "PID", which is an acronym for "Proportional, Integral, Derivative", refers to a type of controller that is designed to eliminate the need for continuous operator attention. Cruise control in a car and a house thermostat are common examples of how PID-based controllers are used to automatically adjust some variable to hold the measurement at the set-point.

The present invention provides structures that embody aspects of the ablation catheter. The present invention also provides RF generators for providing ablation energy to the ablation catheters. The illustrated embodiments discuss these structures and techniques in the context of catheter-based cardiac ablation. These structures, systems, and techniques are well suited for use in the field of cardiac ablation.

However, it should be appreciated that the invention is applicable for use in other tissue ablation applications such as tumor ablation procedures. For example, the various aspects of the invention have application in procedures for ablating tissue in the prostrate, brain, gall bladder, uterus, and other regions of the body, such as regions with an accessible wall or flat tissue surface, using systems that are not necessarily catheter-based. In one embodiment, the target tissue is tumor tissue.

The multifunctional catheters and RF generators of the present invention have advantages over previous prior art devices. The accompanying figures show various embodiments of the ablation systems of the present invention. The present invention is not limited to these particular configurations.

Specific details of electrode and array designs have been given elsewhere, such as in U.S. application Ser. No. 10/997,172, filed Nov. 24, 2004, entitled "Atrial Ablation Catheter and Method of Use", assigned to the assignee of the present invention and herein incorporated by reference in its entirety for all purposes. For the purposes of FIG. 1, it is generally noted that all designs shown may include multiple electrodes, and in some configurations also include a return or ground pad (a large surface area electrode often attached to the patient's back). At least one pair of electrodes, and often many pairs, may be activated or powered with appropriately-powered potential differences to create RF waves that penetrate and ablate desired tissue. If the powering occurs between a pair of electrodes, it is termed "bipolar". If the powering occurs between one electrode and the return pad, it is termed "monopolar". If both bipolar and monopolar power is delivered simultaneously to tissue, it is termed "combo," "combo mode" or "bipolar/monopolar mode."

FIG. 1 shows a schematic depiction of an embodiment of the invention. System 100 includes RF generator (RFG) 10, which is attached to a power source, to ablation catheter 90*a* and also to return pad 80. A source of power, such as AC line voltage of 120V, 220V, etc of single or multiple phase, or a DC source such as an electrochemical battery, is coupled to ablation catheter 90*a* through RF generator (RFG) 10. In an alternative embodiment, the power source, such as the electrochemical battery, is integral to RFG 10, such as to support ambulatory use such as on a battlefield. RFG 10 provides ablation energy to one or more ablation catheters by sending power to one or more independently controlled RF outputs 31 included in RF bank 30. The independent control of each RF output allows a unique, programmable power delivery signal to be sent to each electrode of an ablation catheter. The independent control of each RF output further allows unique (independent) closed loop power delivery, such as power delivery regulated by tissue temperature information received from one or more temperature sensors integral to the attached ablation catheter and/or from sensors included in a separate device.

A multiple wire cable 92 attaches RF bank 30 to the electrodes of ablation catheter 90*a* via electrode connection 91. (The electrodes are not shown but may be metal plates with or without projecting fins that connect to electrode connection 91 via individual wires.) In one embodiment, RF bank 30 includes twelve separate, electrically-isolated RF outputs, grouped into two outputs per channel (six channels total). Each RF output 31 is configured to provide monopolar, bipolar or a combination of monopolar and bipolar currents simultaneously. The number of RF outputs can vary as required by the design. In one embodiment, four to twelve independent RF outputs are provided, such as when the system of the present invention includes a kit of ablation catheters including at least one catheter with from four to twelve electrodes. In another embodiment, more than 16 independent RF outputs are provided, such as when the system of the present invention includes a kit of ablation catheters including at least one catheter with sixteen electrodes.

Monopolar delivery is accomplished by delivering currents that travel from an RF output 41 of bank 40 to an electrically attached electrode of an ablation catheter, through tissue to return pad 80, and back to RFG through connection 11 to which return pad 80 has been connected. Bipolar delivery is accomplished by delivering current between a first RF output 41 which has been electrically connected to a first electrode of an ablation catheter and a second RF output 41 which has been electrically connected to a second electrode of the ablation catheter, the current traveling through the tissue proximate the first and second electrodes. Combo mode energy delivery is accomplished by combining the monopolar and bipolar currents described immediately hereabove.

In one embodiment, simultaneous monopolar and bipolar currents are delivered by utilizing a constant voltage source for all pairs of RF outputs (channels). Varying the voltage phase angle between the paired electrodes can be used to adjust the magnitude of power delivered as well as adjust the ratio of monopolar to bipolar power delivery. The user (e.g. a clinician or clinician's assistant) may select or deselect RF outputs receiving energy to customize therapeutic delivery to an individual patient's needs. In another embodiment, a variable voltage source is applied to the RF outputs. In this embodiment, the voltage phase angle may be fixed (e.g. 0° phase difference for monopolar and 180° phase difference for bipolar). Alternatively, in addition to varying the voltage, the phase angle may be varied. When the phase angle is fixed, the ratio of bipolar to monopolar (or combo to monopolar) may be varied by other means, such as by adjusting the ratio of "cumulative" delivery times of the monopolar versus bipolar (or combo) currents (described in detail in reference to FIGS. 17A-17C, 18A-18B and 19 herebelow).

In another embodiment, five different pre-set energy delivery options are provided to the user: monopolar-only, bipolar-only, and 4:1, 2:1 and 1:1 bipolar/monopolar ratios. A bipolar-only option provides the shallowest depth lesion, followed by 4:1, then 2:1, then 1:1 and then monopolar-only which provides the deepest depth lesion. The ability to precisely control lesion depth increases the safety of the system and increases procedure success rates as target tissue can be ablated near or over important structures. In an alternative embodiment, currents are delivered in either monopolar mode or combo mode (only). The embodiment which avoids bipolar-only, has been shown to provide numerous benefits including reduction of electrical noise generated by switching off the return pad circuit (e.g. to create bipolar-only mode).

In another embodiment, RFG 10 includes multiple independent PID control loops that utilize measured tissue temperature information to regulate (i.e. provide closed loop) energy delivered to an ablation catheter's electrodes. A multiple wire cable 94 attaches temperature sensor input bank 40 to the thermocouples of ablation catheter 90*a* via thermocouple connection 93. (The thermocouples are not shown but may be integral to the electrodes of ablation catheter 90*a* and electrically connected to thermocouple connection 93 via one or more wires.) In one embodiment, multiple wire cable 92 and multiple wire cable 94 are a single conduit. The PID control loops of RFG 10 receive the temperature information via temperature sensor inputs 41 of bank 40. In one embodiment, temperature sensor input bank 40 includes twelve separate, electrically-isolated temperature sensor inputs. Each temperature input 41 is configured to receive temperature information such as from a sensor such as a thermocouple. The number of temperature inputs can vary as required by the design. In one embodiment, four to twelve independent inputs are provided, such as when the system of the present invention includes a kit of ablation catheters including at least one catheter with from four to twelve thermocouples. In another embodiment, more than 16 independent temperature inputs are provided, such as when the system of the present invention includes a kit of ablation catheters including at least one catheter with at least sixteen thermocouples.

Ablation target temperatures are user-selectable and automatically achieved and maintained throughout lesion creation, regardless of blood flow conditions and/or electrode contact scenarios. Temperature target information is entered via user interface 20 of RFG 10. User interface 20 may include a touch screen display, a membrane keypad or other user input components integral to or separate from a housing of RFG 10 (refer to FIG. 21 for a separate remote control configuration). User interface 20 also includes user output components such as text and graphic display screens, indicator lights and other user output components integral to or separate from a housing of RFG 10. User interface 20 is configured to allow an operator to input system parameter and output configuration information including but not limited to: electrode selection; power delivery settings, targets and other power delivery parameters; and other information. User interface 20 is further configured to provide information to the operator, such as visual and audible information including but not limited to: electrode selection, power delivery parameters and other information. Automatic temperature-controlled lesion creation provides safety and consistency in lesion formation. Typical target temperature values made available to the operator range from 50 to 70° C.

In the system of one embodiment, in order to regulate power across a number of separate RF outputs 31 that utilize phase angle differences to generate bipolar currents, the utilization of a constant voltage source, in conjunction with variable duty cycle power delivery, greatly simplifies the control and regulation of power. Utilizing duty cycle power control also provides the ability to deliver high peak powers while providing electrode cooling time during the off-portion of the duty cycle. Duty cycle control is configured such that the period ("on" time plus "off" time) is much less than the thermal time constant of the tissue, such that the tissue acts as an "integrator", continuously accumulating the heat energy while the electrodes of the ablation catheter cool during the off period. In one embodiment, the period of each duty cycle is approximately 17 msec, and the thermal time constant is much longer than 17 msec. Allowing the electrodes to cool during the off period, reduces tissue overheating which could result in "popping" or micro-explosions within the tissue, or other undesired tissue breakdown. Duty cycle periods of approximately 17 msec are applicable to the system of the present invention. Duty cycle periods that are too long result in inadequate ablation of targeted tissue. Duty cycle periods that are too short result in inadequate cooling which may cause char or other blood clots, or damage untargeted tissue. In alternative embodiment, the duty cycle periods may range from 10 msec to 500 msec, and may be adjustable by the operator of the RFG via, e.g., the user interface. Duty cycle energy delivery provides increased efficiency, effectiveness and safety during lesion creation at reduced RMS power levels.

In some embodiments, amplitude control may replace or work in conjunction with duty cycle control. If a fixed duty cycle is implemented, e.g. a 10% duty cycle, the voltage may be regulated (to an amplifier of each RF output 31), such as voltage regulated by the temperature PID loops described above to similarly achieve a target tissue temperature in a precise manner. In an additional embodiment of this varied voltage configuration, if the temperature or power limit can not be reached with a given, pre-set duty cycle, the duty cycle percentage can be increased (e.g. in small steps) until equilibrium is achieved (i.e. the varied voltage, varied duty cycle embodiment mentioned above). The duty cycle percentage chosen provides a power limit (as well as bipolar to monopolar power ratios), and the temperature achieved is regulated by varying RF amplitude (voltage) delivered to RF outputs 31, in monopolar, bipolar, or combo mode energy delivery. In one embodiment, the temperature ratio between the various electrodes can be controlled by adjusting each RF output's duty cycle, such as to balance the temperature across the lesion. By starting with a low duty cycle on-time percentage, and increasing as necessary, power delivery equilibration may be achieved while maximizing the off-time percentage. Maximizing the off-time percentage provides numerous advantages including optimized electrode cooling and tissue temperature equilibrating, as well as maximizing the time that electronic measurements can be made during the low-noise off-time, such as EKG mapping and thermocouple measurements. In some embodiments, this varied voltage control configuration involves the addition of 12 separate variable power supply circuits on RF circuit boards of RFG 10, such as to work with ablation catheters including up to 12 electrodes. The duty cycle percentage is typically set in the range of 5% to 25% depending upon the (tissue) load resistance and power required for adequate ablation. This voltage-varied configuration is an alternative method of power control that can give the same or similar clinical effects to the duty cycle power control described above.

Figure 4:
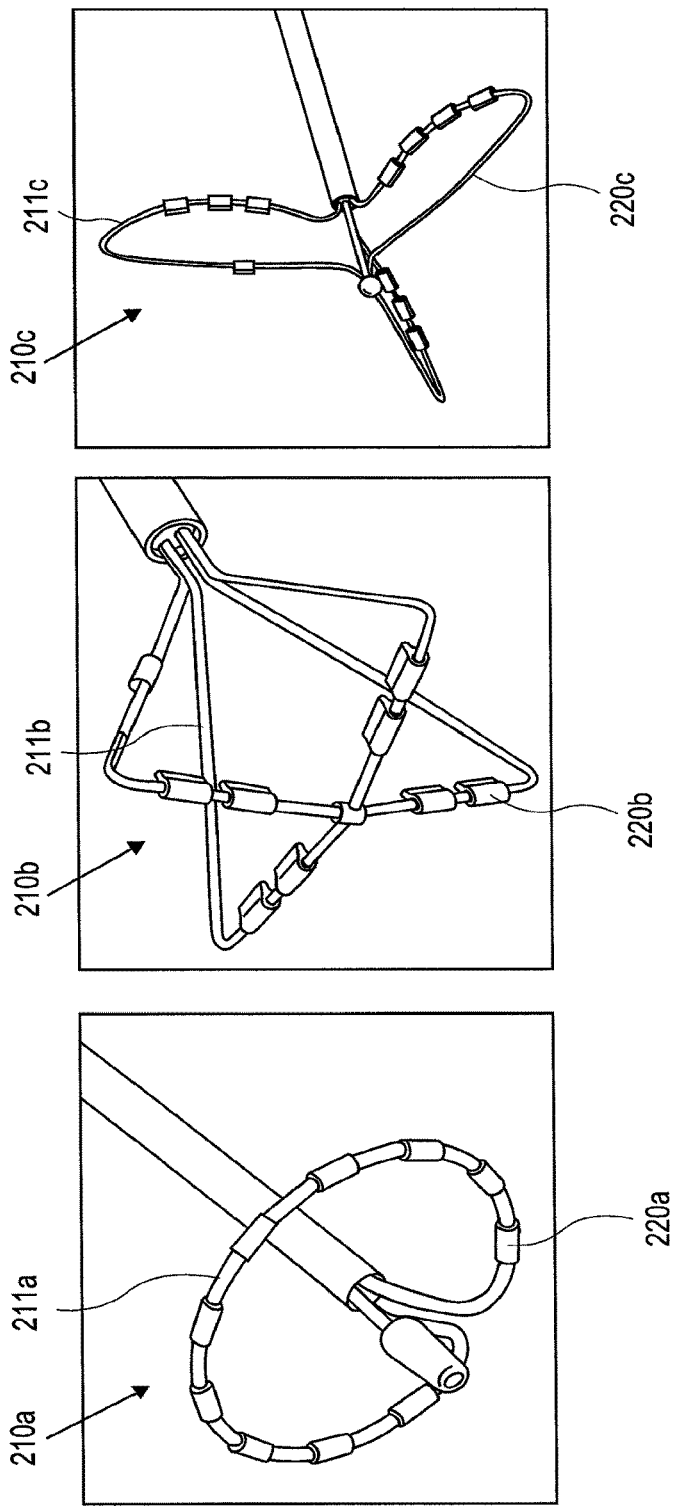
FIGS. 4A, 4B and 4C illustrate perspective views of electrode carrier assemblies of three different ablation catheters, consistent with the present invention.

Referring back to FIG. 1, system 100 further includes ablation catheter 90*b* and ablation catheter 90*c*, each of which is configured to attach to RF output bank 30 and temperature sensor input bank 40 for energy delivery and temperature feedback similar to that described above in reference to ablation catheter 90*a*. Ablation catheters 90*a*, 90*b* and 90*c* may be of the construction described herebelow in reference to FIGS. 4A, 4B and 4C respectively. Alternative or additional ablation catheters may be included in the system of the present invention.

More details on the system of the present invention are provided below.

Figure 2:
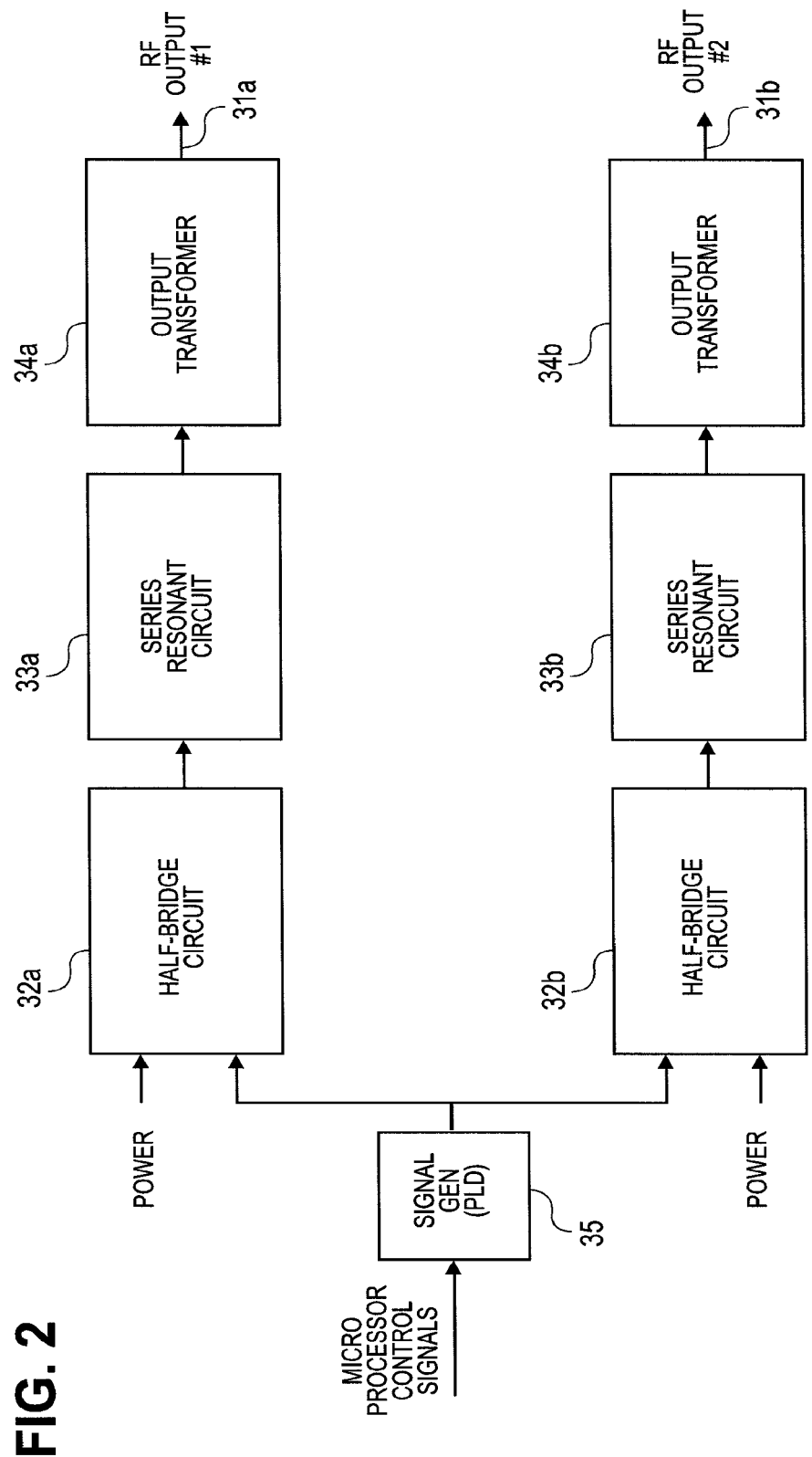
FIG. 2 illustrates details of a portion of the embodiment of FIG. 1, including a pair of RF outputs.

Referring to FIG. 2, power from the power source of FIG. 1 is used to digitally generate a high-power, low-voltage, low-frequency square wave. FIG. 2 illustrates two parallel circuits which produce a first RF output 31*a* and a second RF output 31*b*, such as a pair of RF outputs (a channel)—used to deliver bipolar energy to a pre-determined pair of electrodes on an ablation catheter. The parallel circuits for RF output 31*a* and RF output 31*b* include half-bridge circuits 32*a* and 32*b*, series resonant circuits 33*a* and 33*b*, and output transformers 34*a* and 34*b*, respectively. Half-bridge circuits 32*a* and 32*b* each receive a drive signal from signal generator 35, such as a programmable logic device (PLD). Signal generator 35 receives control signals from a microprocessor of the RFG of the present invention.

Figure 3:
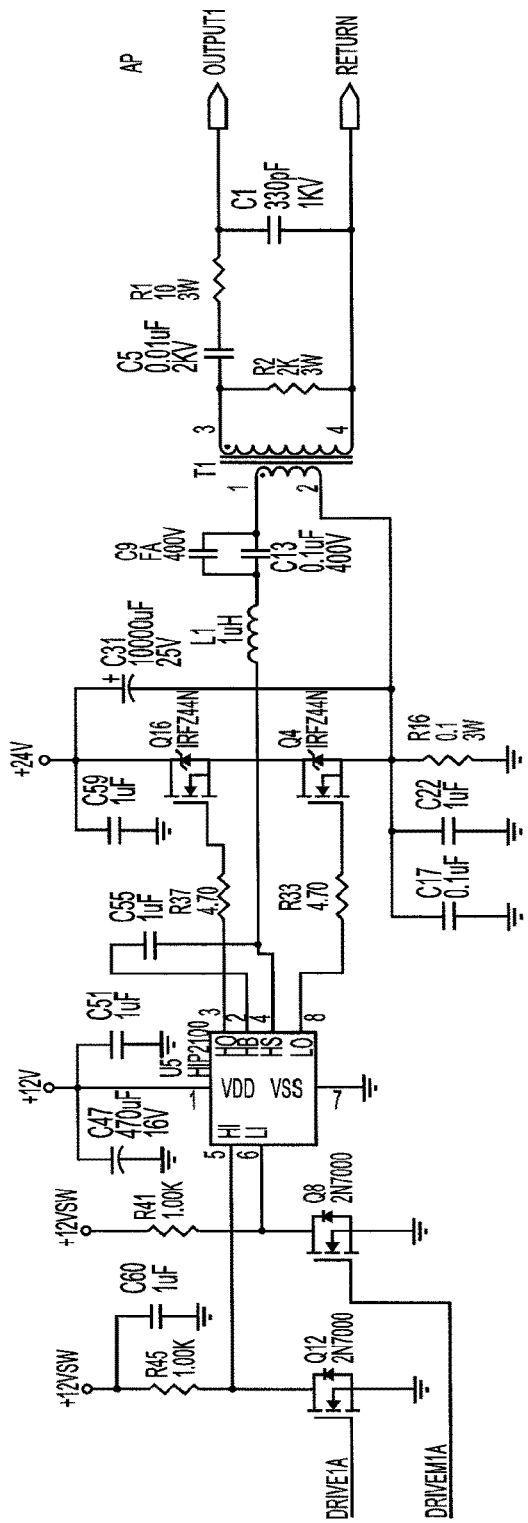
FIG. 3 illustrates a circuit diagram of an RF output of FIG. 2.

Half bridge circuits 32*a* and 32*b* each produce a square wave, e.g. a 24-volt peak-to-peak square wave. Series resonant circuits 33*a* and 33*b* each couple the high power square wave to output transformers 34*a* and 34*b* respectively. Output transformers 34*a* and 34*b* each is an isolation transformer configured to provide both patient electrical isolation and the voltage step-up required to ablate tissue. In more detail, the ablation electrodes are at patient potential, and 5000-6000 volts isolation is provided between the electrodes and earth ground. Since the input is at chassis ground, output transformers 34*a* and 34*b* each is configured to provide 5000-6000 volts isolation between its primary and secondary coils. An additional advantage of this isolation circuitry is that power can be measured without the need to isolate the measuring devices. A portion of the applicable circuitry is shown in FIG. 3.

Series resonant circuits 33*a* and 33*b* each convert the square ware received from half bridge circuits 32*a* and 32*b* respectively, to a sine wave. These conversions are accomplished by maximizing energy coupling at the fundamental frequency chosen, e.g., at 470 kHz. This power output configuration is over 95% efficient in converting the 24 VDC input power to RF energy, as the output transformer has an efficiency close to 100%. In this configuration, half-bridge circuit 32*a* and 32*b*, series resonant circuit 33*a* and 33*b* and output transformer 34*a* and 34*b*, are configured to convert signal generator's 45 470 kHz logic level signal to two 100 VAC sine waves, each capable of delivering 100 watts. In addition, it is noted that by measuring power inputted ($P_{input}$), outputted power ($P_{output}$) may be obtained. In one embodiment, a current-sensing resistor is employed (not shown, but having a precise, known resistance) so inputted current ($I_{in}$) can be determined by the system. Since inputted voltage ($V_{in}$) is also known, as the power supply precisely regulates this, the system can determine $P_{in}$ and thus $P_{output}$.

As noted above, the system employs a frequency of 470 kHz (or approximately 470 kHz, noting that 500 kHz is not used as it may be reserved for a public emergency band.)

The 470 kHz is generated by a PLD, signal generator 35. In particular, an oscillator provides (starts with) a higher frequency, which is then divided down to 470 kHz. The 470 kHz waveform may be generated in numerous configurations, such as with 0° phase or any other phase, such as a phase determined in 250 steps or divisions. In one embodiment, the signal for the PLD is a 5-volt digital signal with the phase information "built-in". Signal generator 35 also generates the opposite polarity signal which may also be used to drive one or more field effect transistors (FETs) integral to half bridge circuit 32a and 32b. Signal generator 35 provides a synchronization pulse, not shown but connected to the signal generators of subsequent pairs of RF outputs also not shown; such that all the signal generators of the RFG are in synchrony (i.e. signal generator 35 is the "master").

In one embodiment, an RF circuit board includes two circuits of FIG. 2, i.e. two signal generator 35's, four half bridge circuits 32's, four series resonant circuits 33's and four output transformers 34's, producing four RF outputs (or two channels). In this configuration, 2 RF boards would provide 8 RF outputs and 3 RF boards would provide 12 RF outputs.

Signal generator 35 is under microprocessor control. In one embodiment, the microprocessor can set the duty cycle from all "off" to all "on" in at least 16 steps, and possibly 256 steps. In another embodiment, the microprocessor can adjust the phase of the RF output can be set from 0° to 180° in at least 4 steps, and possibly 16 steps. This adjustability allows the energy to flow to pairs of electrodes in the following ways: all monopolar from the electrodes to the return pad; all bipolar between the electrodes; and a combination of bipolar and monopolar with the ratio set by the phase difference between the electrodes.

Referring now to FIG. 3, a schematic of one configuration of an RF output circuit is illustrated. Possible values for components are listed on the figure. Transformer T1 is an isolation transformer. Resistor R2, e.g., approximately 2000 ohms, provides a static load across the RF amplifier circuitry and improves the stability of the signal during light load conditions.

Referring now to FIG. 4A, a distal portion of an ablation catheter of the system of the present invention is illustrated. Carrier assembly 210a includes a single carrier arm 211a with multiple electrodes 220a (e.g. 10 electrodes) mounted along its length. Each electrode is constructed of a conductive material, such as platinum, and typically has a mass between 20 and 50 milligrams, or between 30 and 40 milligrams. Each electrode 220a may include a thermocouple, not shown, but integral to electrode 220a and proximate the tissue contacting surface of electrode 220a. The thermocouples may be small mass thermocouples, typically less than 200 micrograms or less than 100 micrograms, such as to provide fast and accurate tissue/electrode interface temperatures. In one embodiment, the thermocouples integral to electrodes 220a are made of 38 gauge wire and have a mass between 48 and 88 micrograms, typically 68 micrograms. Carrier assembly 210a can be adjusted to transition between a near-linear geometry to the near-helical geometry shown in FIG. 4A. Carrier assembly 210a may be configured for making contact with a pulmonary vein ostium of a patient.

Referring now to FIG. 4B, a distal portion of an ablation catheter of the system of the present invention is illustrated. Carrier assembly 210b includes multiple electrodes 220b (e.g. 8 electrodes) mounted to four carrier arms 211b arranged in an umbrella configuration. The tissue contacting portion of electrodes 220b face away from the proximal end of the ablation catheter such that pushing forward carrier assembly 210b advances the tissue contacting portion of electrodes 220b into tissue. Each electrode is constructed of a conductive material, such as platinum, and typically has a mass between 17 and 37 milligrams, such as approximately 27 milligrams. Each electrode 220b may include a thermocouple, not shown, but integral to electrode 220b and proximate the tissue contacting surface of electrode 220b. The thermocouples may be small mass thermocouples, typically less than 200 micrograms or less than 100 micrograms, such as to provide fast and accurate tissue/electrode interface temperatures. In one embodiment, the thermocouples integral to electrodes 220b are made of 40 gauge wire and have a mass between 22 and 62 micrograms, typically 42 micrograms. Each electrode 220b may include a projecting fin as shown, configured to provide a heat sink into circulating blood. Carrier assembly 210b can be adjusted to transition between a near-linear geometry to the umbrella geometry shown in FIG. 4B. Carrier assembly 210b may be configured for making contact with the far wall of the left or right atrium of the heart of a patient.

Referring now to FIG. 4C, a distal portion of an ablation catheter of the system of the present invention is illustrated. Carrier assembly 210c includes multiple electrodes 220c (e.g. 12 electrodes) mounted to three carrier arms 211c arranged in an umbrella configuration. The tissue contacting portion of electrodes 220c face toward the proximal end of the ablation catheter such that pulling carrier assembly 210c advances the tissue contacting portion of electrodes 220c into tissue. Each electrode is constructed of a conductive material, such as platinum, and typically has a mass between 17 and 37 milligrams, such as approximately 27 milligrams. Each electrode 220c may include a thermocouple, not shown, but integral to electrode 220c and proximate the tissue contacting surface of electrode 220c. The thermocouples may be small mass thermocouples, typically less than 200 micrograms or less than 100 micrograms, such as to provide fast and accurate tissue/electrode interface temperatures. In one embodiment, the thermocouples integral to electrodes 220c are made of 38 gauge wire and have a mass between 48 and 88 micrograms, typically 68 micrograms. Each electrode 220c may include a projecting fin as shown, facing away from the proximal end of the ablation catheter and configured to provide a heat sink into circulating blood. Carrier assembly 210c can be adjusted to transition between a near-linear geometry to the umbrella geometry shown in FIG. 4C. Carrier assembly 210c may be configured for making contact with the septum of the left atrium of the heart of a patient.

The ablation catheters of FIGS. 4A, 4B and 4C are each ablation catheters configured to receive energy from the RF generator of the present invention. Additional and/or alternative catheters may also be configured to receive energy from the RF generator of the present invention. Each of the ablation catheters of FIGS. 4a, 4B and 4C may include a thermocouple within each electrode. Alternatively or additionally, one or more carrier arms include a thermocouple along its length, such as midway between two electrodes. Placement of the thermocouple in the electrode is such that during ablation, thermocouples are located directly over the target tissue at a distance separated by the electrode wall thickness only (such as a wall thickness of 0.006" or alternatively a wall thickness ranging from 0.004" to 0.010"). The combination of thermocouple location, size and mounting methods provides fast and accurate tissue/electrode interface temperatures. Type T thermocouples (copper/ constantan) may be employed as the temperature accuracy curve for type T is essentially linear within the temperature range used by the ablation system, i.e., body temperature through 80° C.

Figure 5:
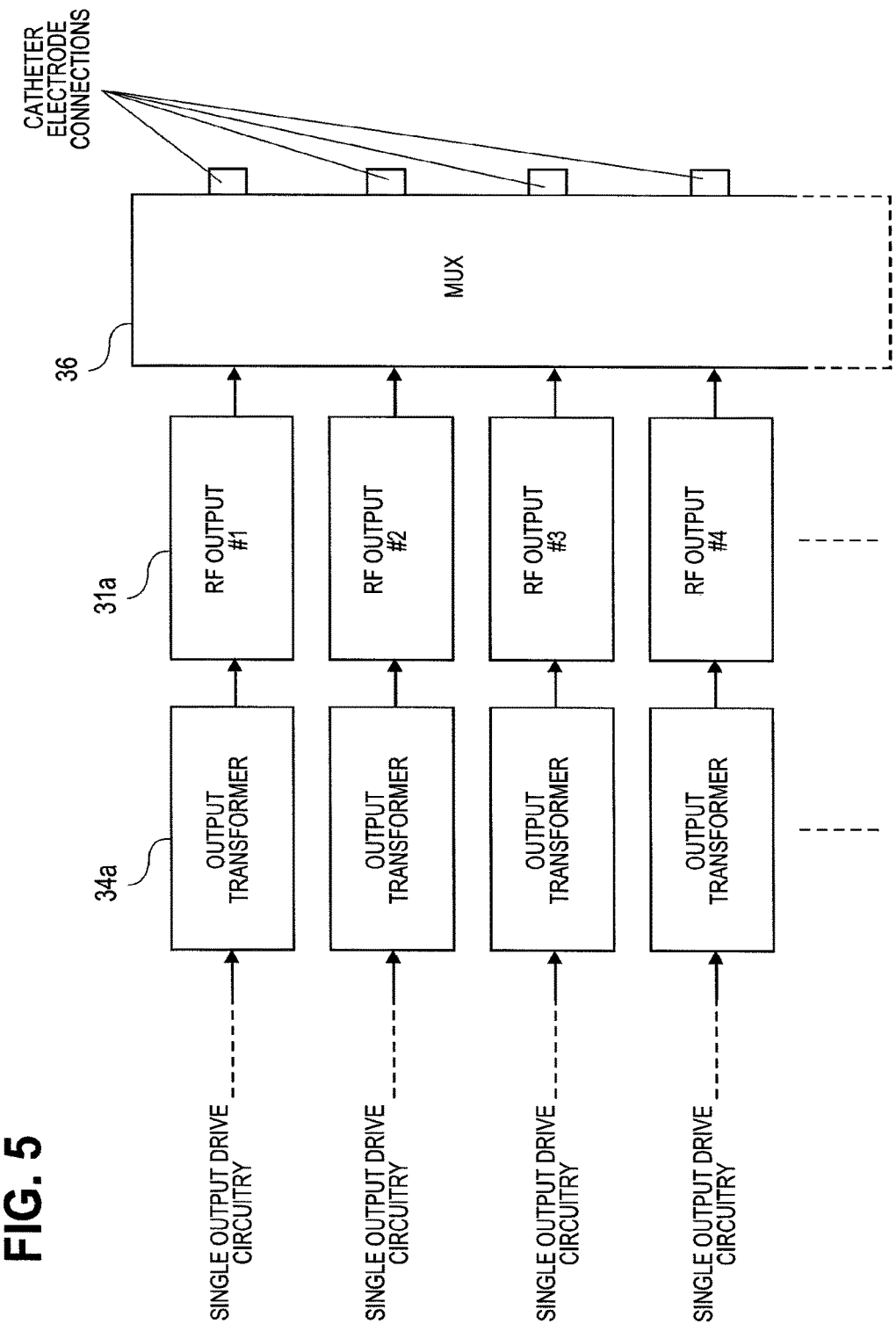
FIG. 5 illustrates a schematic depiction of an RF output portion of an RF generator, including multiplexed outputs, consistent with the present invention.

Referring now to FIG. 5, another configuration of the present invention is illustrated in which the RF Generator's independent RF outputs can be selectively connected to the electrodes of one or more ablation catheters. Multiple outputs transformers, such as output transformer 34a, each of which produces an independent RF output, such as RF output 31a, are connected to multiplexer 36. Multiplexer 36 includes circuitry to selectively connect each RF output to one of a bank of connections, each of which is electrically connected to one or more electrodes of an ablation catheter. Via a user interface of the RF generator, not shown, the operator can select which RF outputs are connected to which electrodes, such as to deliver bipolar or combo energy to any pair of electrodes.

Referring additionally to FIGS. 6A and 6B, arrays of electrodes on the carrier assemblies of two different ablation catheters are illustrated. In FIG. 6A, carrier assembly 210a includes four carrier arms 211a on which eight electrodes are fixedly mounted. In FIG. 6B, carrier assembly 210b includes three carrier arms 211b on which twelve electrodes are fixedly mounted. Using the multiplexing circuitry of FIG. 5, any pairs of electrodes may receive bipolar energy such as electrode pair "1-2" or "2-4" of carrier assembly 210a of FIG. 6A, or electrode pair "3-4" or "4-12" of carrier assembly 210b of FIG. 6B. All combinations of energy delivery are enabled by the independent control of each RF output combined with the electrode selectivity provided by multiplexer 36 and associated circuitry of FIG. 5. The energy delivered can be customized based on individual patient requirements. In one configuration, energy delivery may start on the outermost electrodes (e.g. 1, 3, 6 and 8 of FIG. 6A and 1, 5 and 9 of FIG. 6B), and drive power to the center. In another configuration, the centermost electrodes (e.g. 2, 4, 5 and 7 of FIG. 6A and 4, 8 and 12 of FIG. 6B) receive energy simultaneously. In yet another configuration, the linearly aligned electrodes of FIG. 6A or FIG. 6B deliver energy to produce a circular lesion. In yet another configuration, a first electrode mounted to a first carrier arm transmits bipolar energy to a second electrode mounted to a second carrier arm.

Referring now to FIGS. 7A and 7B, two schematic representations of multiple electrode assemblies and a return pad each in contact with patient tissue are shown. Referring for FIG. 7A, if four separate RF outputs of the same voltage and phase were connected to Electrode 1, Electrode 2, Electrode 3, and Electrode 4, and the return pad connected to RF Generator ground, there would be current flow through tissue portions T1, T2, T3 and T4. There would be zero current flow through tissue portions T5, T6 and T7. On the other hand, if four separate RF outputs of all different voltages were connected to Electrode 1, Electrode 2, Electrode 3, and Electrode 4 and the return pad was disconnected (i.e. not connected to RF generator ground), there would be current flow through tissue Portions T5, T6 and T7. Due to the disconnected ground pad, there would be no current flow through tissue portions T1, T2, T3 and T4. Finally, if four separate RF outputs of the same voltage were connected from Electrode 1, Electrode 2, Electrode 3, and Electrode 4 to the return pad, and there were phase differences between each electrode, there would be current flow through tissue portions T1, T2, T3 and T4 and there would also current flow through tissue portions T5, T6 and T7.

Example: Combination Monopolar-Bipolar RF Delivery Method

In the example shown in FIG. 7B, if there were 40 volts RMS delivered between Electrode 5 and the return pad 0° phase, and 40 volts RMS delivered between Electrode 6 and the return pad at 180° phase, then tissue portions T8 and T9 would have 40 RMS volts across them resulting in a power in each tissue portion of 16 watts RMS (Power=$V^2$/R=(40× 40)/100)—where each tissue portion is modeled at 100 ohms of impedance). The phase difference between Electrode 5 and Electrode 6 would cause a potential difference of 80 volts. The resulting power across tissue portion T10 would be 64 watts RMS. (Power=$V^2$/R=(80×80)/100). By varying the phase difference between Electrode 5 and Electrode 6 from 0° to 180°, the power delivered can be varied from 0 to 80 watts RMS.

In one embodiment, the generation of the combined bipolar and monopolar currents is achieved by varying the phase, as described above. In an alternative embodiment, the combined bipolar and monopolar currents are determined by time-division multiplexing and/or by alternating monopolar and bipolar fields, as will be described in detail in reference to subsequent figures.

In one exemplary system, repeating duty cycle fields are employed, each field having a similar period (duration) and each field including an "on" portion and an "off" portion. A possible field period is approximately 17 msec. During the on period, 20-100 volts RMS (typically 100 volts RMS) is delivered to the tissue. During the off period, the output of the channel is disconnected from the load. In one embodiment, a sequence of four specific duty cycle fields that repeat are provided. A first field includes monopolar energy delivery only followed by an off period; the second field includes combined monopolar and bipolar delivery (combo) followed by an off period; the third field includes monopolar energy delivery only followed by an off period; and the fourth field includes monopolar and bipolar delivery (combo), with opposite phase from that of field 2, followed by an off period. In one embodiment, by selecting the phase difference during a field, the ratio between bipolar and monopolar energy delivery can be varied from 4-to-1 to all-monopolar. Also, by switching off the connection to the return pad, and setting the phase shift to 180°, an all-bipolar mode can be produced.

Phasing Sequences

In one embodiment, the ablation signal delivered to each electrode pair from two associated RF outputs (channel) includes four fields (e.g. each of 17 ms period), the four fields repeating until ablation energy delivery is terminated. Each field is divided into an "on" time and an "off" time. This duty cycle ratio controls the amount of power delivered during each field by that RF output pair (channel). In one embodiment, during the "on" time, 100 volts RMS (at 470 kHz) is delivered to the load. During the "off" time, the output is floating, thus zero power is delivered. For example, a duty cycle of 10% would cause a power of 10 watts RMS to be delivered into a 100 ohm load during the duty cycle period (e.g. a field with 17 msec duration). If the voltages to the two electrodes are at a 0° phase difference, the bipolar voltage difference is zero volts and therefore only monopolar currents will be delivered. If the phase difference is 90°, the bipolar voltage difference is 1.414 times the monopolar voltage ($E_{MONOPOLAR}$), thus the power delivered is twice the monopolar power, as shown in the equation:

$$\text{Power} = E^2/R = (1.414 * E_{MONOPOLAR})^2/R = 2*(E_{MONOPOLAR})^2/R$$

If the phase difference is 180°, the voltage difference is 2 times the monopolar voltage, thus the power delivered is four times the monopolar power, as shown in the equation:

$$\text{Power} = E^2/R = (2*E_{MONOPOLAR})^2/R = 4*(E_{MONOPOLAR})^2/R$$

If the return pad is off, then only bipolar currents will be delivered. Field sequences such as are shown in FIGS. 8-12 may be used to achieve various bipolar to monopolar power ratios.

During each field, each RF output pair (channel) may deliver RF power in monopolar, bipolar or combo energy delivery. Each field may include "on" time ratios (monopolar, bipolar or combo) from 0% to 100% of the duty cycle period, typically 17 msec. In one embodiment, each energy delivery includes at least monopolar energy delivered, avoiding the need to disconnect the return pad. Continuous connection of the return pad avoids generation of electrical noise, and allows the inclusion of safety detection circuitry which requires connection of the return pad.

Figures 8A, 8B, 8C, 8D:
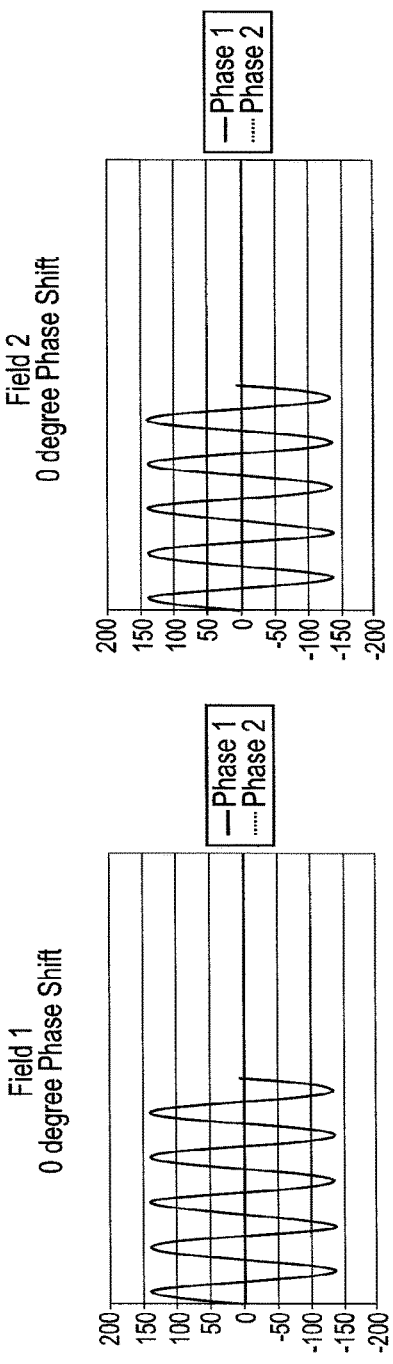
FIG. 8A-D illustrate a power delivery scheme including four fields configured to deliver only monopolar power, consistent with the present invention.
Figure 10A:
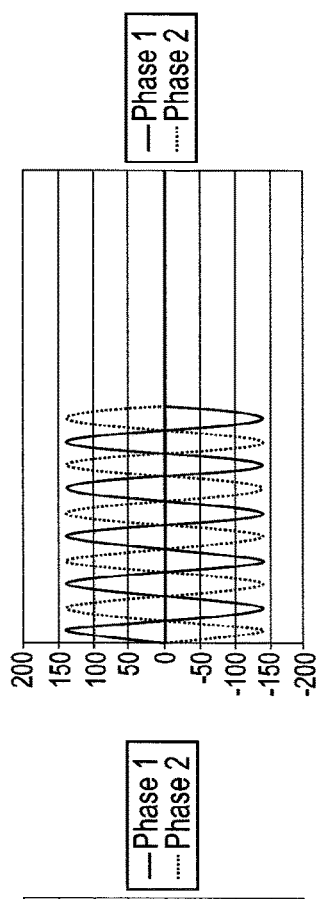
FIG. 10A-D illustrate a power delivery scheme including four fields configured to deliver a 2:1 ratio of bipolar to monopolar power, consistent with the present invention.
Figure 10B:
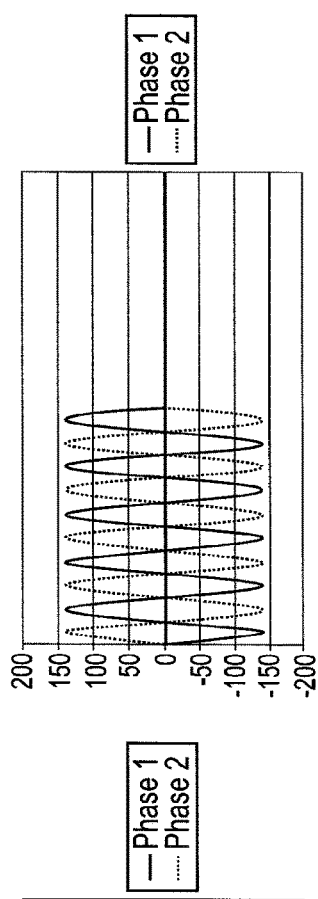
Figure 10C:
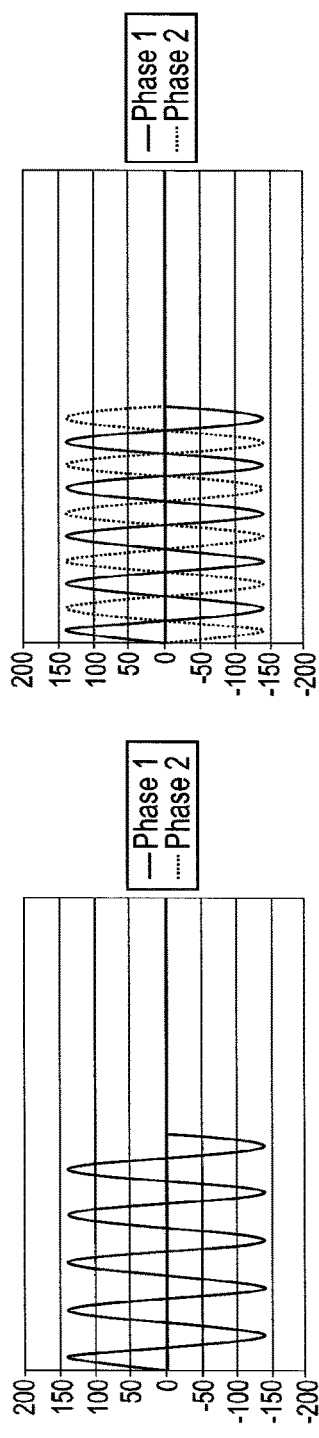
Figure 10D:
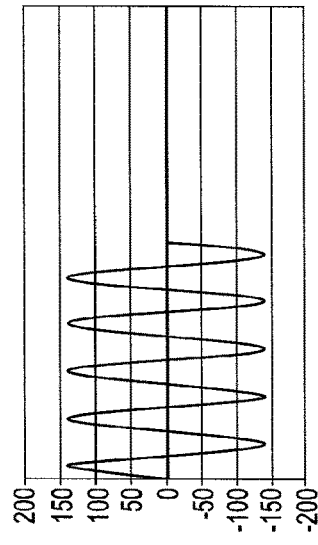
Figure 11A:
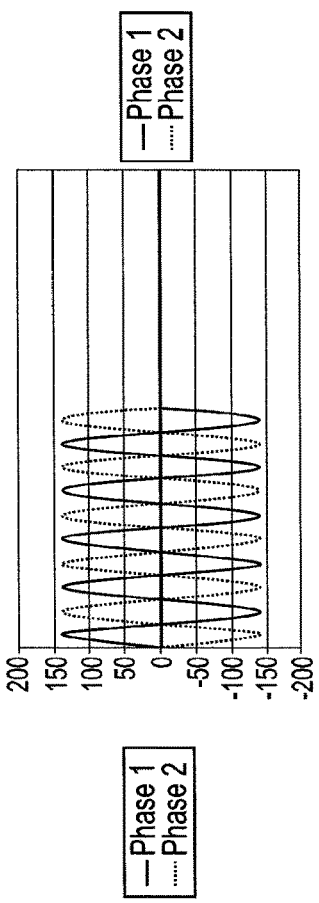
FIG. 11A-D illustrate a power delivery scheme including four fields configured to deliver a 4:1 ratio of bipolar to monopolar power, consistent with the present invention.
Figure 11B:
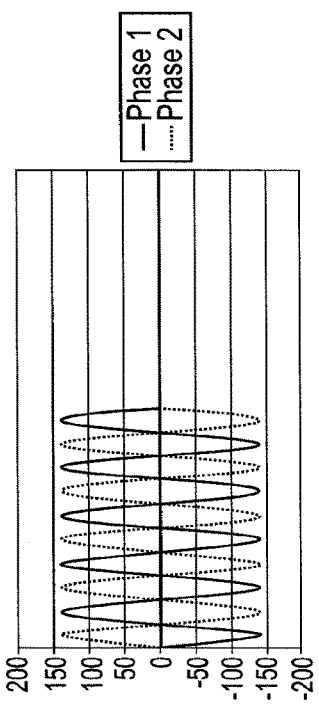
Figure 11C:
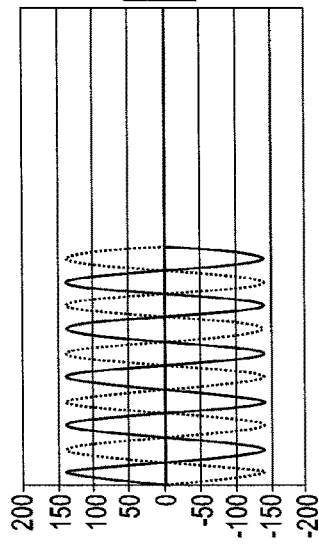
Figure 11D:
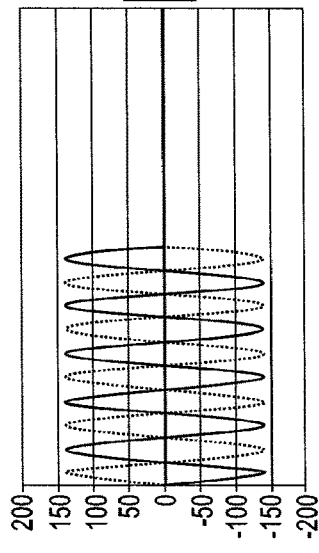
Figure 12A:
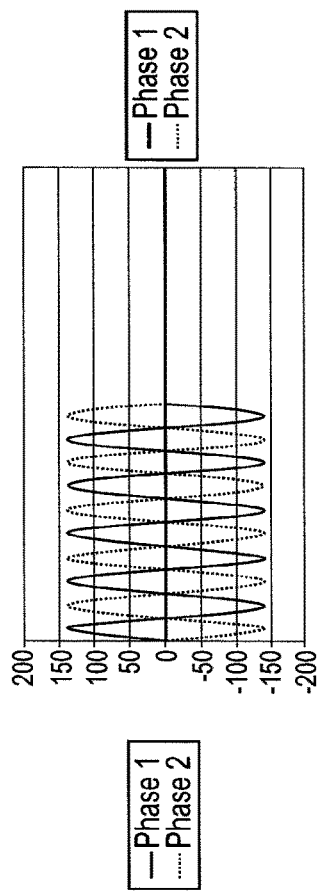
FIG. 12A-D illustrate a power delivery scheme including four fields configured to deliver only bipolar power, consistent with the present invention.
Figure 12B:
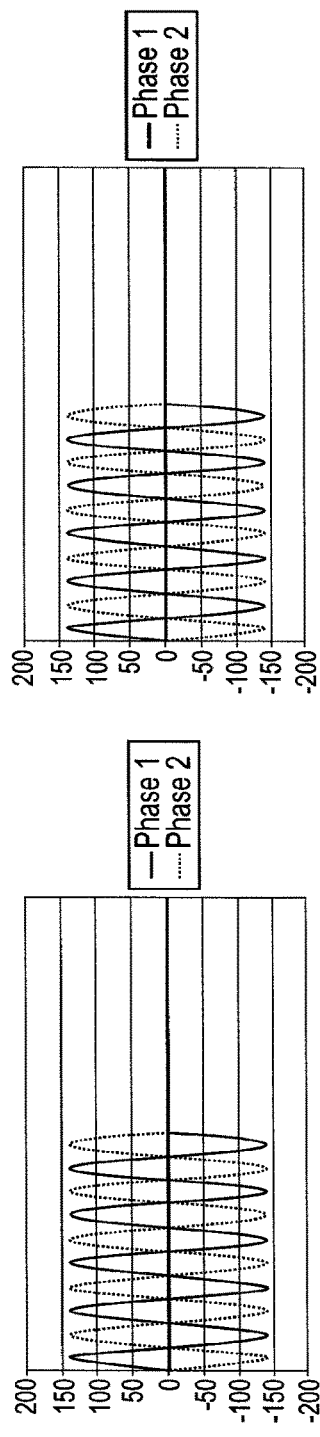
Figure 12C:
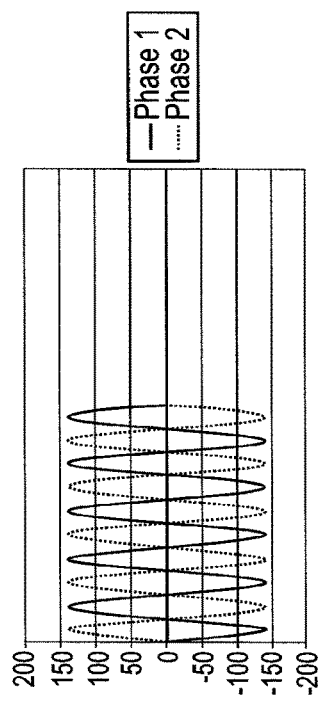
Figure 12D:
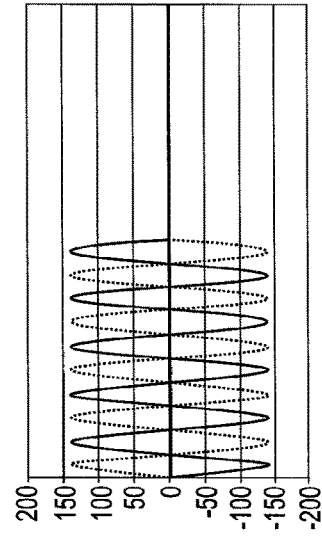

Referring now to FIG. 8, a repeating sequence of four fields configured to deliver monopolar power (only) to an RF output pair, or channel, is illustrated. The RF output pair receiving energy is connected to a pair of electrodes on an attached ablation catheter. During the "on" time, typically 100 volts RMS (at 470 kHz) is delivered to the tissue (load) in contact with the electrodes of the ablation catheter. During the "off" time, the output is floating, thus zero power is delivered. The return pad is connected during all four fields, maintained at 0 volts and receives the monopolar currents from each electrode delivering monopolar energy. Typically, all four fields have a 17 msec duty cycle period. The four fields repeat until the set ablation time is reached, or an alarm or alert condition is identified. All four fields have 0° phase shift between the two RF outputs (no bipolar energy delivery) causing monopolar energy to be delivered to the tissue in contact with the electrode pair during each of the four fields.

Referring now to FIG. 9, a repeating sequence of four fields configured to deliver a 1:1 ratio of bipolar to monopolar power to an RF output pair, or channel, is illustrated. The RF output pair receiving energy is connected to a pair of electrodes on an attached ablation catheter. During the "on" time, typically 100 volts RMS (at 470 kHz) is delivered to the tissue (load) in contact with the electrodes of the ablation catheter. During the "off" time, the output is floating, thus zero power is delivered. The return pad is connected and maintained at 0 volts during all four fields, and receives the monopolar currents from each electrode delivering monopolar energy. Typically, all four fields have a 17 msec duty cycle period. The four fields repeat until the set ablation time is reached, or an alarm or alert condition is identified. Field 1 and Field 3 have 0° phase shift between the two RF outputs (no bipolar energy delivery) causing monopolar energy to be delivered to the tissue in contact with the electrode pair during the "on" time of Field 1 and Field 3. Field 2 and Field 4 have a 90° phase shift between the two RF outputs such that bipolar energy is delivered between the electrodes connected to the two RF outputs. Since the return pad is connected (as it is in Fields 1 and 3), monopolar energy is also delivered in Fields 2 and 4 (combo mode). As has been described above, the 90° phase shift causes twice the amount of bipolar energy as monopolar energy to be delivered, during that field where both are delivered. With the duty cycle percentage held constant in all four fields (same "on" time versus "off" time ratio), the bipolar power delivered in two fields (Fields 2 and 4 with the 90° phase shift) equates to the same power delivered in four fields of monopolar power delivery (Fields 1-4), thus the 1:1 ratio.

Referring now to FIG. 10, a repeating sequence of four fields configured to deliver a 2:1 ratio of bipolar to monopolar power to an RF output pair, or channel, is illustrated. The RF output pair receiving energy is connected to a pair of electrodes on an attached ablation catheter. During the "on" time, typically 100 volts RMS (at 470 kHz) is delivered to the tissue (load) in contact with the electrodes of the ablation catheter. During the "off" time, the output is floating, thus zero power is delivered. The return pad is connected and maintained at 0 volts during all four fields, and receives the monopolar currents from each electrode delivering monopolar energy. Typically, all four fields have a 17 msec duty cycle period. The four fields repeat until the set ablation time is reached, or an alarm or alert condition is identified. Field 1 and Field 3 have 0° phase shift between the two RF outputs (no bipolar energy delivery) causing monopolar energy to be delivered to the tissue in contact with the electrode pair during the "on" time of Field 1 and Field 3. Field 2 and Field 4 have a 180° phase shift between the two RF outputs such that bipolar energy is delivered between the electrodes connected to the two RF outputs. Since the return pad is connected (as it is in Fields 1 and 3), monopolar energy is also delivered in Fields 2 and 4 (combo mode). As has been described above, the 180° phase shift causes four times the amount of bipolar energy as monopolar energy to be delivered, during that field where both are delivered. With the duty cycle percentage held constant in all four fields (same "on" time versus "off" time ratio), and four times the bipolar power delivered as monopolar in Fields 2 and 4, two fields of bipolar at a 180° phase shift (Fields 2 and 4) equates to twice the power delivered in four fields of monopolar (Fields 1-4), thus the 2:1 ratio.

Referring now to FIG. 11, a repeating sequence of four fields configured to deliver a 4:1 ratio of bipolar to monopolar power to an RF output pair, or channel, is illustrated. The RF output pair receiving energy is connected to a pair of electrodes on an attached ablation catheter. During the "on" time, typically 100 volts RMS (at 470 kHz) is delivered to the tissue (load) in contact with the electrodes of the ablation catheter. During the "off" time, the output is floating, thus zero power is delivered. The return pad is connected and maintained at 0 volts during all four fields, and receives the monopolar currents from each electrode delivering monopolar energy. Typically, all four fields have a 17 msec duty cycle period. The four fields repeat until the set ablation time is reached, or an alarm or alert condition is identified. All fields (1-4) have a 180° phase shift between the two RF outputs such that bipolar energy is delivered between the electrodes connected to the two RF outputs. Since the return pad is connected, monopolar energy is also delivered in all fields (combo mode). As has been described above, the 180° phase shift causes four times the amount of bipolar energy as monopolar energy to be delivered, during that field where both are delivered. Since all the fields are configured the same, the 4:1 ratio is delivered.

Referring now to FIG. 12, a repeating sequence of four fields configured to deliver only bipolar power to an RF output pair, or channel, is illustrated. The RF output pair receiving energy is connected to a pair of electrodes on an attached ablation catheter. During the "on" time, typically 100 volts RMS (at 470 kHz) is delivered to the tissue (load) in contact with the electrodes of the ablation catheter. During the "off" time, the output is floating, thus zero power is delivered. The return pad is disconnected, preventing monopolar energy delivery. Typically, all four fields have a 17 msec duty cycle period. The four fields repeat until the set ablation time is reached, or an alarm or alert condition is identified. All fields (1-4) have a 180° phase shift between the two RF outputs such that bipolar energy is delivered between the electrodes connected to the two RF outputs. Since the return pad is disconnected, no monopolar energy is delivered in any field. Alternatively, the RF generator can be operated in bipolar-only mode with the return pad can be left connected by adjusting the phase angles such that ensure that all current flows only between the ablation electrodes and none flows to the return pad.

In FIGS. 8-11, all fields include monopolar power delivery such that the return pad is never switched off. The power delivery schemes illustrated in FIGS. 9-12 utilize a phase shift adjustment between two RF outputs to control the ratio of bipolar to monopolar power delivery. The system of the present invention is configured to independently provide similar or dissimilar fields of energy delivery to other provided channels, such as RF output pairs connected to 4, 8, 12, 16 or more electrodes of an ablation catheter. Additional variables may be controlled to modify the bipolar-monopolar ratio, total power delivered, or other output parameter, such variables including but not limited to: duty cycle percentage; duty cycle period; applied voltage; frequency of applied voltage; shape of applied voltage such as sinusoidal, triangle wave or square wave; connection to the return pad; voltage applied to return pad; and combinations thereof.

The system of the present invention allows independent phase control of each RF output (e.g. up to 16 outputs or more), providing more sophisticated power delivery as compared to a previously developed system in which every other channel was driven at the same phase and each RF output drove two electrodes. Each of the RF outputs can be driven up to a maximum power, and ablation energy can be sent to each RF output simultaneously or sequentially. The ability to control the phase of each electrode relative to the other electrodes enables the system to generate bipolar currents as well as monopolar, as well as various combinations of these.

In the system of the present invention, each RF channel may utilize independent PID loops which process temperature information (e.g. temperature information received from a thermocouple mounted in each electrode) to modify the power delivery to that pair of RF outputs. These PID loops provide more accurate temperature-driven energy delivery than previously developed systems. One previously developed system delivered power to 12 electrodes based on temperature feedback from three zones. The electrodes were regulated to the highest temperature in the zone, which resulted in some of the electrodes ablating inefficiently (e.g. not enough power delivered).

Figure 13:
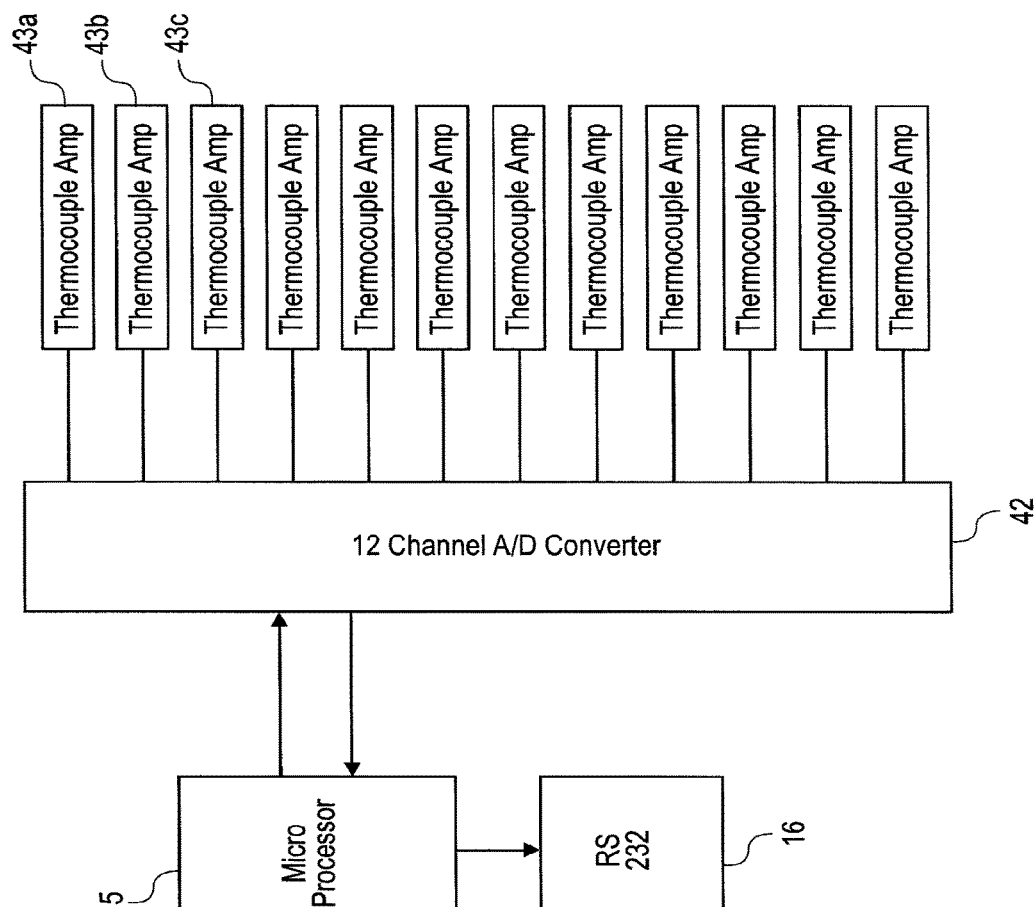
FIG. 13 illustrates a schematic depiction of a temperature sensor input portion of an RF generator, consistent with the present invention.

Referring now to FIG. 13, an exemplary embodiment of temperature sensor input circuitry is illustrated. Twelve separate, isolated, temperature acquisition modules include twelve thermocouple amplifiers, 43a, 43b, 43c, etc., which are configured to electrically connect to up to twelve thermocouples of one or more ablation catheters of the present invention. The thermocouples may be small mass thermocouples, typically less than 200 micrograms or less than 100 micrograms, such as to provide fast and accurate tissue/electrode interface temperatures. The twelve thermocouple amplifiers 43a, 43b, 43c, etc are electrically connected to a twelve channel analog to digital (A/D) converter 42. A/D converter 42 is electrically connected to microprocessor module 15. An RS-232 module 16 is electrically connected to microprocessor module 15.

Fast and accurate temperature acquisition is important in delivering the proper amount of RF energy (i.e. closed-loop control). Too much (high) energy delivery can cause coagulum and/or damage adjacent tissues and structures such as the phrenic nerve or the esophagus of the patient. Too little energy delivery can result in poor lesion creation and low therapeutic success rates. The system of the present invention provides enough RF energy to create a cardiac electrical conduction block without affecting adjacent tissues or structures. In order to acquire fast and accurate temperatures, the thermocouple mass is kept small and one or more electrodes are welded directly to the inside diameter of each of the electrodes of each ablation catheter. Placement of the thermocouple in the electrode is such that during ablation, thermocouples are located directly over the target tissue at a distance separated by the electrode wall thickness only (such as a wall thickness of 0.006" or alternatively a wall thickness ranging from 0.004" to 0.010"). The combination of thermocouple location, size and mounting methods provides fast and accurate tissue/electrode interface temperatures. Type T thermocouples (copper/constantan) may be employed as the temperature accuracy curve for type T is essentially linear within the temperature range used by the ablation system, i.e., body temperature through 80° C.

All thermocouples located on the ablation electrodes are at patient potential. 5000 volts of isolation is needed between the thermocouples and earth ground in order to meet patient safety regulations (e.g. IEC 601-2). The twelve temperature modules are read by microprocessor module 15 which is powered by a dc-to-dc converter with the proper voltage isolation. An RS232 serial data string is isolated with an opto-isolator. Since the RF power output is duty cycle-controlled, the temperature readings can be synchronized to the "off" period of each field. The synchronizing pulse is also supplied through an opto-isolator.

Figure 14:
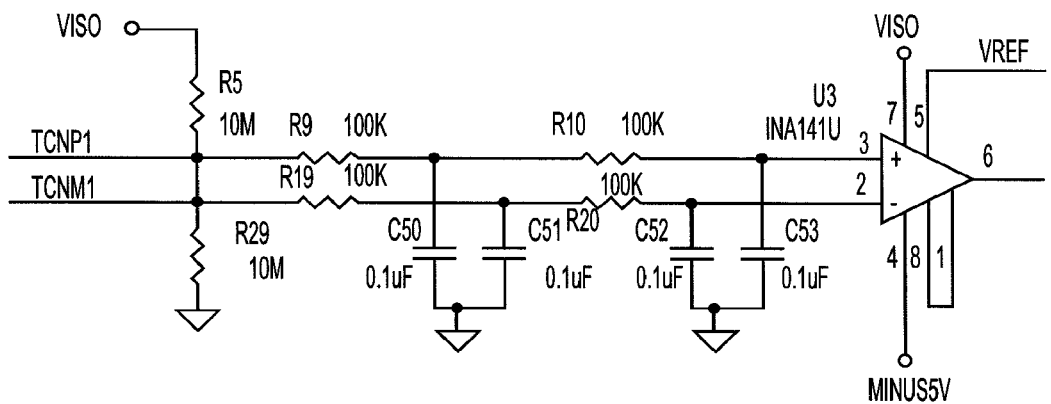
FIG. 14 illustrates a circuit diagram of a temperature sensor input portion of an RF generator, consistent with the present invention.

Referring additionally to FIG. 14, a schematic of a thermocouple amplifier circuit is shown. Each temperature module makes use of a true instrumentation amplifier with a precision DC gain of 100 and several poles of RC low pass filtering configured to attenuate the 470 kHz ablation voltage. A high-impedance DC bias voltage provides an indication of when the (very low-resistance) thermocouple is not present.

Basic Power Control Scheme

Figure 15:
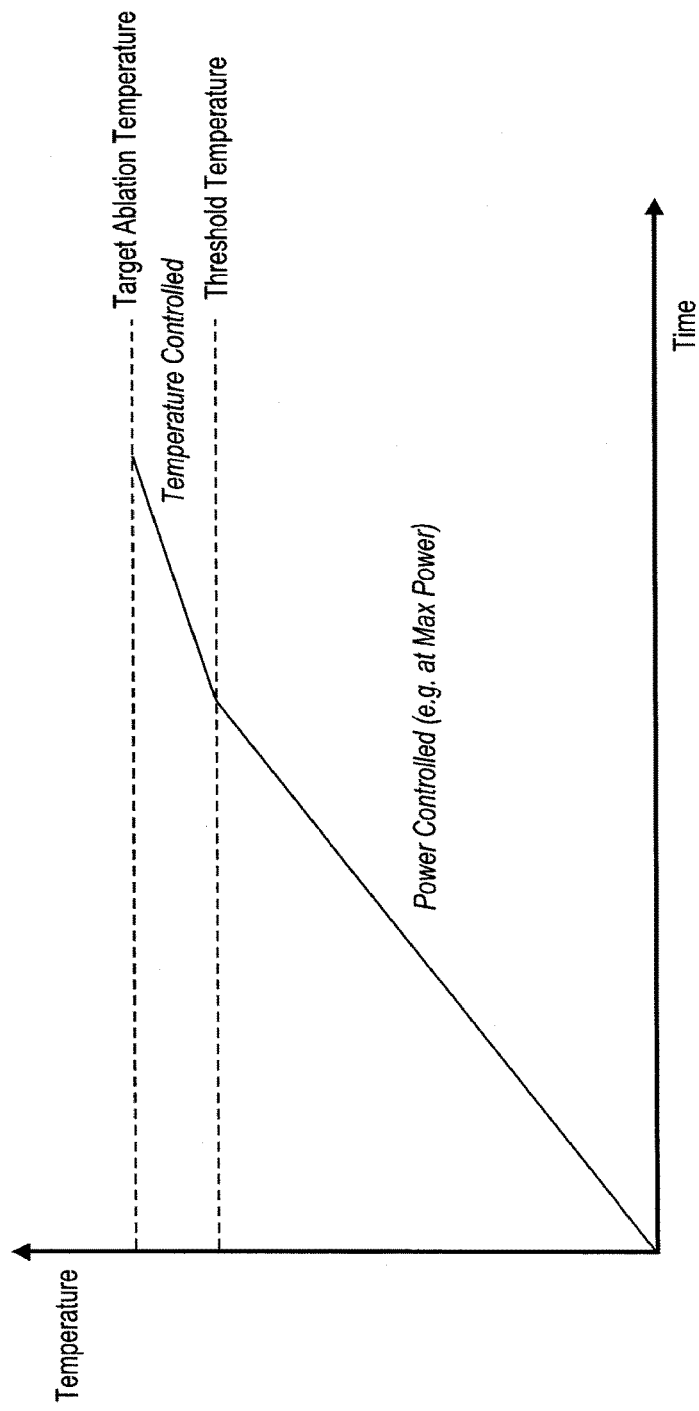
FIG. 15 illustrates a power delivery scheme for an RF generator, consistent with the present invention.

Referring now to FIG. 15, one embodiment of energy delivery is illustrated in which dual, sequentially implemented algorithms are employed to control power delivered. This method of energy delivery can be applied independently to each RF output, or each RF channel (pair of RF outputs). When an ablation catheter's electrodes are cool (e.g. at body temperature) and thus far from a user-programmed target temperature (e.g. greater than 5° C. from a target ablation temperature) as measured by the system's thermocouples or other temperature sensors, energy delivery may be generated at a fixed level of power, irrespective of temperature sensed by the thermocouples or other temperature sensors (first algorithm). In one embodiment, a maximum level of power (e.g. $P_{max}$=16 watts) may be delivered. When the temperature reaches a predetermined temperature band (e.g., T<5° C. from the target temperature), the system changes from fixed (e.g. maximum) power level delivery to energy delivery controlled to temperature (second algorithm where power delivery is regulated by a temperature control loop). When in the temperature control loop, the system changes the duty cycle ("on" time/"off" time ratio) to allow the tissue temperature to controllably progress to the desired target temperature, such as to minimize or prevent overshoot. In an alternative embodiment, the threshold temperature at which the second algorithm is implemented, is also set by the user through, e.g., the user interface. In other words, in addition to the target temperature, a threshold temperature is also set by the user, instead of a fixed amount such as the 5° C. mentioned above.

In one embodiment, the duty cycle (field) period is approximately 16-17 msec, such that if 10 watts RMS power is to be delivered for a specific field (entire length) and 100 watts RMS is delivered during the "on" period, the "on" period duration would be set to 1.7 msec and the "off" period duration would be set to 15.3 msec. A typical duty cycle may be about 10%, and a typical voltage applied may be about 100 volts RMS. If the nominal load (impedance of the tissue) is about 100 ohms, this 10% duty cycle would yield 100 watts RMS for the 17 msec period. In any case, a target temperature between 50° C.-70° C. (e.g., 60° C.) may be set, and the system may deliver energy to heat and ablate as described in reference to FIG. 15.

Figure 16:
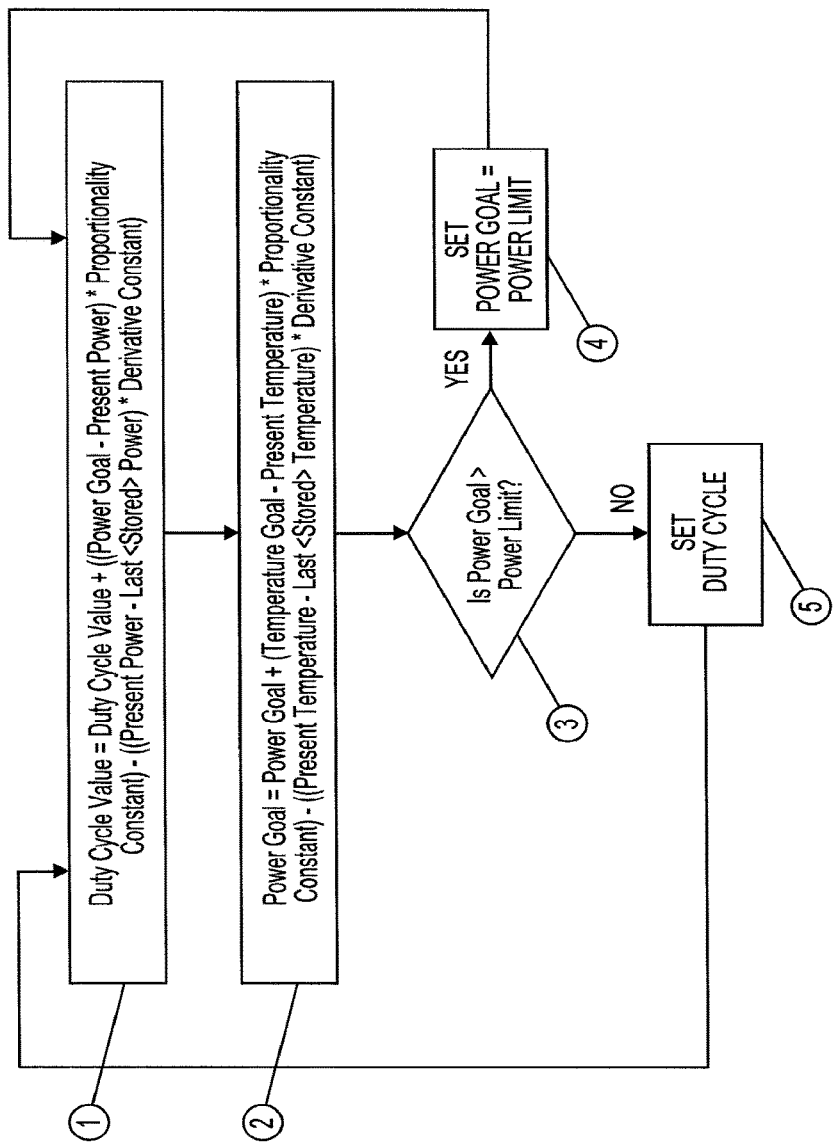
FIG. 16 illustrates a power delivery algorithm for an RF generator, consistent with the present invention.

Referring now to FIG. 16, a flow chart of another power control algorithm is illustrated. This method of energy delivery can be applied independently to each RF output, or each RF channel (pair of RF outputs). The control method uses a main control loop and a secondary control loop. The main loop controls the duty cycle and compares the actual power to a power goal. The proportional difference between the goal and the actual power is added to an integration register. The difference between the last power delivered and the present power (the derivative) is subtracted from the integration register. The new value in the integration register sets the duty cycle value.

The secondary control loop controls the power goal and compares the actual temperature (measured) to a temperature goal. The proportional difference between the goal and the actual temperature is added to an integration register. The difference between the last temperature measured and the present temperature (the derivative) is subtracted from the integration register. The value in the integration register sets the power goal value. If the power goal value is greater than the power limit, the power goal is set to equal the power limit.

The algorithm of FIG. 16 provides a safe and efficient way of delivering power to create a lesion, and is particularly effective at limiting overshoot of achieved temperature (above the target temperature).

In the algorithm of FIG. 16, if the target temperature is reached prior to reaching a maximum power, the ablation may occur without ever delivering the maximum power. If the target temperature is not achieved, the system will limit power delivery to a maximum power. In one embodiment, an algorithm applies a set of power limits specific to the bipolar-monopolar ratio used. For one or more ablation catheters of the present invention, this set of power limits is as listed in Table 1 below:

TABLE 1

| Bipolar-Monopolar Ratio | Power Limits |
| --- | --- |
| Monopolar-only | 10 Watts RMS |
| 1:1 | 10 Watts RMS |
| 2:1 | 10 Watts RMS |

TABLE 1-continued

| Bipolar-Monopolar Ratio | Power Limits |
| --- | --- |
| 4:1 | 8 Watts RMS |
| Bipolar-only | 6 Watts RMS |

Figure 17A:
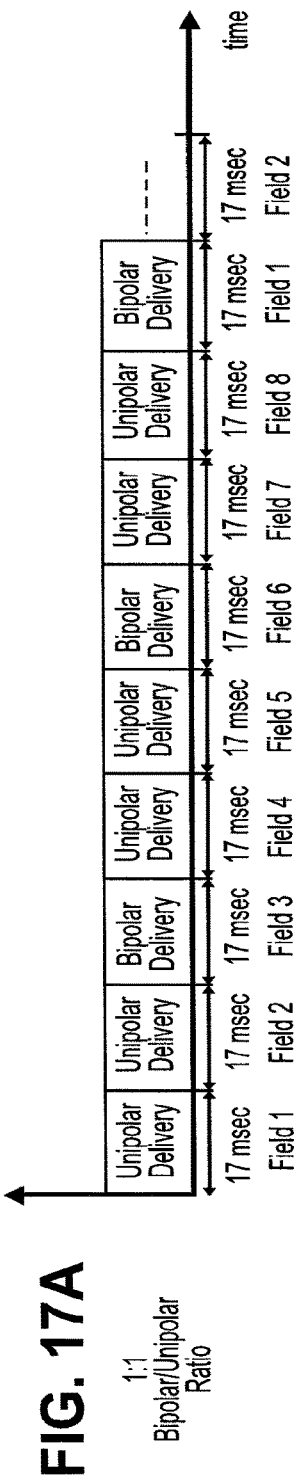
FIGS. 17A, 17B and 17C illustrates power delivery schemes in which the bipolar to monopolar ratio is set by varying the ratio of bipolar to monopolar fields, consistent with the present invention.
Figure 17B:
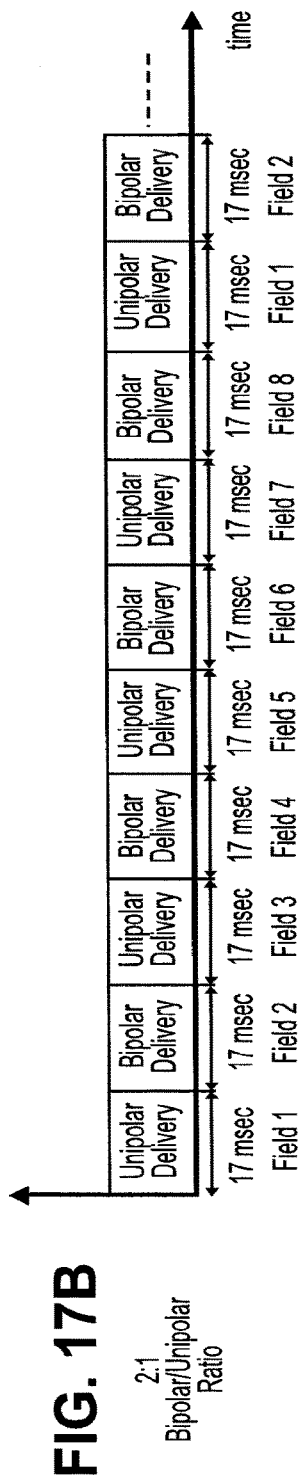
Figure 17C:
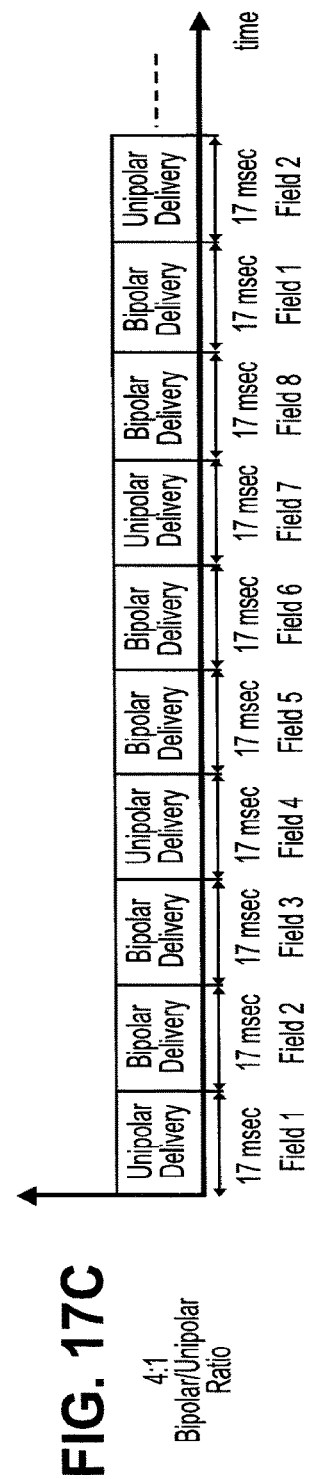

Referring now to FIGS. 17A, 17B and 17C, an algorithm for setting the ratio of bipolar to monopolar energy delivery is illustrated. The bipolar to monopolar energy delivery ratio is varied by adjusting the number (ratio) of monopolar to bipolar fields. Held constant are the duty cycle ("on" time and "off" time lengths), the field length (17 msec) and the bipolar delivery phase angle. In this embodiment, the phase angle is set to 90° such that bipolar energy is twice monopolar energy delivery at the same applied voltage, as has been described above. Referring specifically to FIG. 17A, a 1:1 ratio of bipolar to monopolar energy delivery is achieved with a 1:2 ratio of bipolar to monopolar fields (e.g. a set of two monopolar fields followed by one bipolar field, which repeat). Referring specifically to FIG. 17B, a 2:1 ratio of bipolar to monopolar energy delivery is achieved with a 1:1 ratio of bipolar to monopolar fields (e.g. a set of one monopolar field followed by one bipolar field, which repeat). Referring specifically to FIG. 17C, a 4:1 ratio of bipolar to monopolar energy delivery is achieved with a 2:1 ratio of bipolar to monopolar fields (e.g. a set of one monopolar field followed by two bipolar fields, which repeat). In an alternative embodiment, the bipolar to monopolar ratio is further adjusted by varying one or more of duty cycle, field length and phase angle. In another alternative embodiment, one or more bipolar fields are replaced with combo fields.

Referring now to FIGS. 18A 18B, another algorithm for setting the ratio of bipolar to monopolar energy delivery is illustrated. The bipolar to monopolar energy delivery ratio is varied by adjusting duty cycle ("on" time and "off" time lengths). Held constant are the ratio of bipolar to monopolar fields (set to 1:1), the field length (17 msec) and the bipolar delivery phase angle. In this embodiment, the phase angle is also set to 90° such that bipolar energy is twice monopolar energy delivery at the same applied voltage, as has been described above. Referring specifically to FIG. 18A, a 2:1 ratio of bipolar to monopolar energy delivery is achieved with a 1:1 ratio of bipolar to monopolar "on" times. In both the bipolar and monopolar fields, the duty cycle is set to 50%, or 8.5 msec of the 17 msec period. Referring specifically to FIG. 18B, a 4:1 ratio of bipolar to monopolar energy delivery is achieved with a 2:1 ratio of bipolar to monopolar "on" times. In both the bipolar field, the "on" time is 10 msec (approx 58% duty cycle) and in the monopolar field the "on" time is 5 msec (approx 29% duty cycle). In an alternative embodiment, the bipolar to monopolar ratio is further adjusted by varying one or more of the ratio of bipolar to monopolar fields, field length and phase angle. In another alternative embodiment, one or more bipolar fields are replaced with combo fields.

Figure 19:
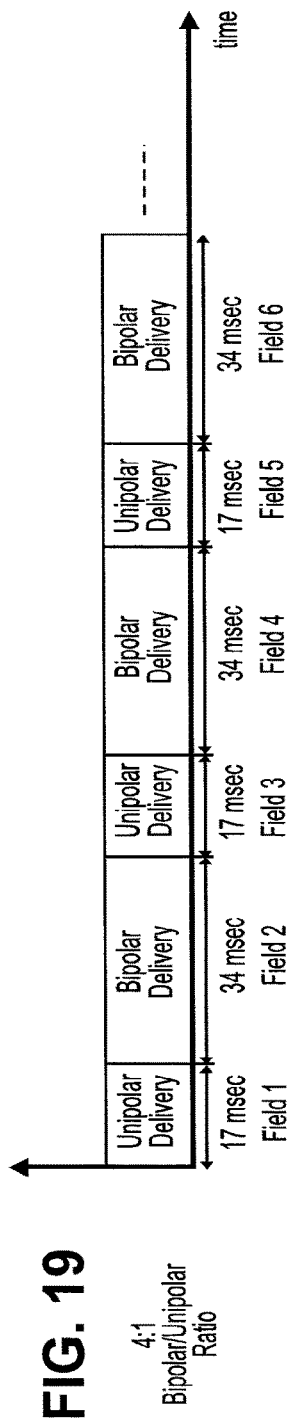
FIG. 19 illustrates a power delivery scheme in which the bipolar to monopolar ratio is set by varying the length (time) of the bipolar and/or monopolar fields, consistent with the present invention.

Referring now to FIG. 19, another algorithm for setting the ratio of bipolar to monopolar energy delivery is illustrated. The bipolar to monopolar energy delivery ratio is varied by adjusting field length. Held constant are the ratio of bipolar to monopolar fields (set to 1:1), the duty cycle (within the fields—e.g. 10%) and the bipolar delivery phase angle. In this embodiment, the phase angle is also set to 90° such that bipolar energy is twice monopolar energy delivery at the same applied voltage, as has been described above. A 4:1 ratio of bipolar to monopolar energy delivery is achieved with a 2:1 ratio of bipolar to monopolar field lengths (e.g. 34 msec to 17 msec respectively). In an alternative embodiment, the bipolar to monopolar ratio is further adjusted by varying one or more of the ratio of bipolar to monopolar fields, field length and phase angle. In another alternative embodiment, one or more bipolar fields are replaced with combo fields.

In the embodiments of FIGS. 17A-C, 18A-B and 19, the applied voltage is also held constant. In alternative embodiments, the voltage is varied to modify the ratio of bipolar to monopolar power delivered. In the embodiments of FIGS. 17A-C, 18A-B and 19, some fields include the delivery of bipolar energy. In alternative embodiments, these bipolar energy delivery fields are replaced with combo energy delivery, and the associated variables mathematically adjusted to achieve the desired bipolar to monopolar ratio.

Figure 20:
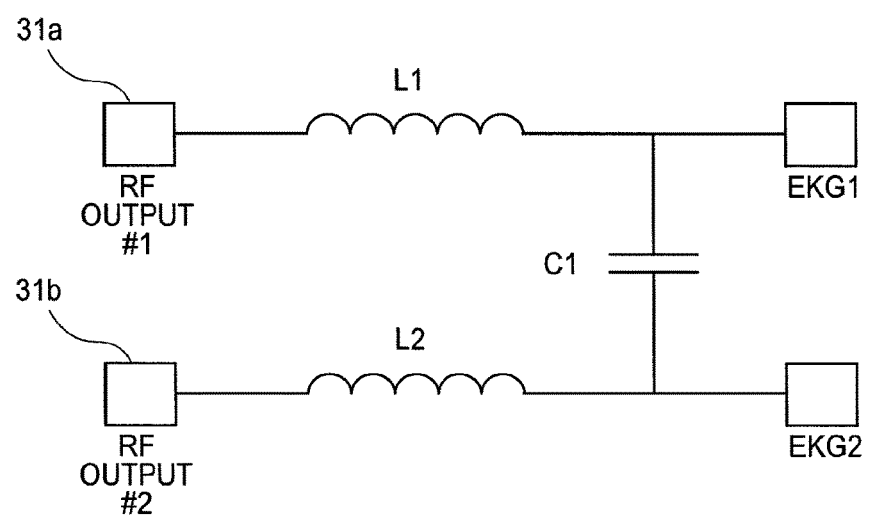
FIG. 20 illustrates a schematic of an exemplary embodiment for interfacing RF outputs with an EKG diagnostic device.

Referring now to FIG. 20, a schematic of an embodiment for interfacing RF outputs with an EKG diagnostic device is illustrated. It is important that the RF energy delivered is "isolated" from an EKG diagnostic device or module (such as a separate EKG monitor or an EKG monitor integrated into the RF generator of the present invention). A resistor, such as a 10 Kohm resistor in series with the output, can be used to attenuate the RF power yet let the mapping information pass through. The issue with such a configuration is the mapping information is also attenuated dramatically. In the embodiment of FIG. 20, a 1000 milliHenry inductor L1, is placed between the RF output 31a and the input to the EKG module EKG1. The inductor provides sufficient attenuation of the high frequency RF signal (e.g. 3300 ohms of impedance with RF delivered at 470 kHz as has been described above), yet very low impedance in the lower frequency spectrum representing EKG information. A second inductor L2, is placed between second RF output 31b and a second input to the EKG module EKG2. A capacitor C1 is placed between EKG1 and EKG2, completing a low-pass filter which reduces the RF voltage that is "exposed" to an attached EKG diagnostic device. Inductors can be placed between each RF output (i.e. connected to each electrode of an ablation catheter) and an associated EKG diagnostic device input.

Figure 21:
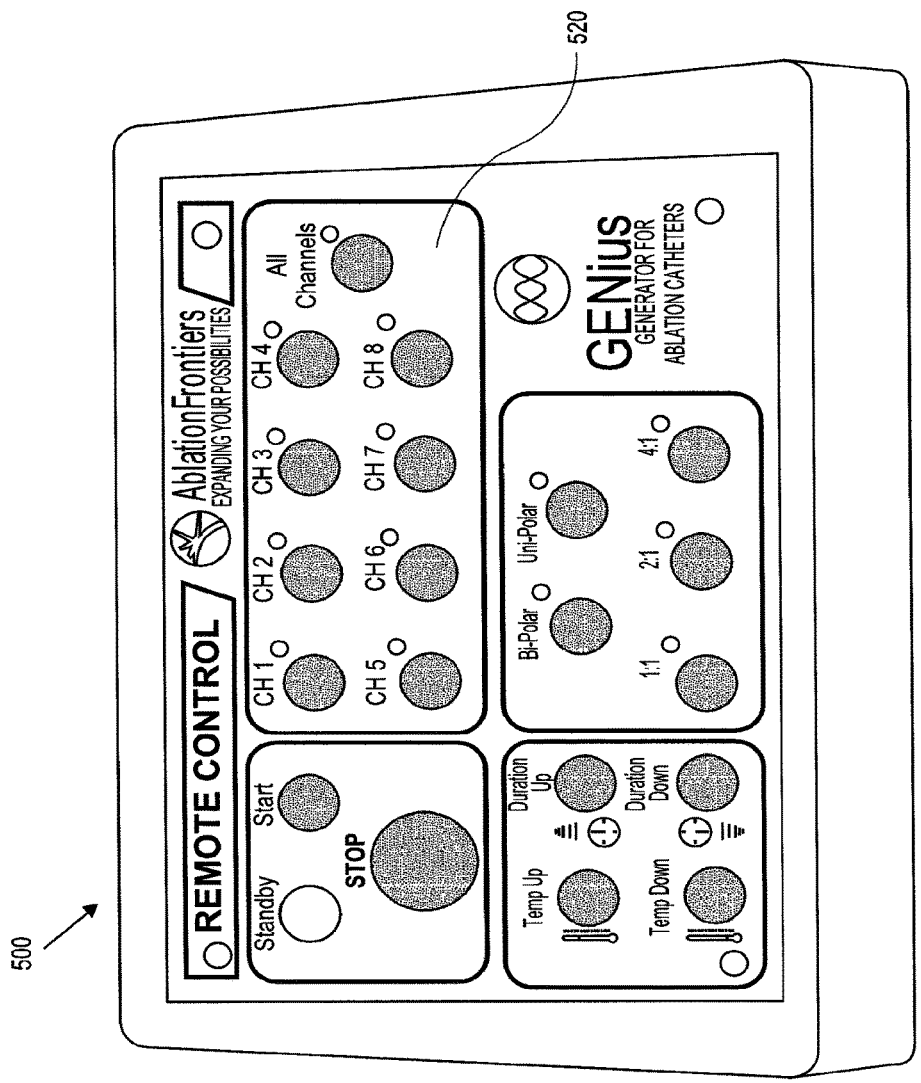
FIG. 21 illustrates an exemplary remote control for an RG generator.

Referring now to FIG. 21, an embodiment of a remote control for the RF generator is illustrated. Remote control 500 is configured to send commands to an RFG of the present invention, via information input into user interface 520 by an operator of the system. User interface 520 is configured to allow an operator to input system parameter and output configuration information including but not limited to: electrode selection; power delivery settings, targets and other power delivery parameters; and other information. User interface 520 may be further configured to provide information to the operator, such as visual and audible information including but not limited to: electrode selection, power delivery parameters and other information.

In one embodiment, remote control 500 provides full control of the RFG of the present invention, such that no other user interface is required to perform any and all functions of the RFG. In an alternative embodiment, remote control 500 provides partial control of the RFG. User interface 520 may replace a user interface integral to an RFG, or work in combination with it. In one embodiment, user interface 520 is the master control, overriding conflicting commands from a user interface of the RFG. In another embodiment, the user interface of the RFG is the master control. User interface 520 includes a bank of switches, such as a membrane keypad, and/or other user input components, to enter commands to be received by the RFG. User interface 520 further includes user output components such as indicator lights, displays such as LCD displays, and other means of presenting information to an operator of the RFG. In one embodiment, user interface 520 includes a touch screen display configured to provide information to the user and receive commands from the user.

Remote control 500 includes a housing 501, such as a plastic housing which surrounds one or more electronic modules and includes user interface 520 on its top, outer surface. In one embodiment, a bundle of wires connect remote control 500 to the RFG of the present invention, such as via a ten pin receptacle integral to the housing of the RFG. In an alternative embodiment, remote control 500 includes a wireless transceiver, not shown but possibly configured to send and receive wireless transfer of information to and from the RFG, such as via a handshaking protocol which assures accuracy of information transfer. Remote control 500 may be provided sterilized and/or may be covered with a disposable sterile bag, not shown, but configured to surround remote control 500 and at least a portion of any wires attached to remote control 500. The sterile assembly may be brought into the sterile field of a patient undergoing a sterile procedure, such as a cardiac ablation procedure to treat atrial fibrillation, or a tumor ablation procedure.

The systems of the present invention may include one or more power limits which can be integrated into software and/or hardware of the RFG. The system may employ different power limits for different ablation catheters. Alternatively or additionally, the system may employ different power limits for different bipolar-monopolar ratios. In one embodiment, the system includes power limits from Table 1 above. In one embodiment, different power limits (or sets of power limits as shown in the above table) are used for different ablation catheters. Alternatively or additionally, power limits of 20-30 Watts RMS may be used by one or more algorithms for one or more ablation catheters of the present invention. In general, ablation catheters with larger electrodes may correlate to a higher power limit than an ablation catheter with smaller electrodes. The power limits are employed to limit clinician error as well as otherwise improve safety, such as by reducing the likelihood of coagulum creation or ablation of untargeted tissue. It has been demonstrated that in the instance where one or more electrodes has limited or otherwise inadequate tissue contact, such as when a "hotspot" in the tissue may have been caused, the above power limits were successful in avoiding the creation of coagulum.

The system of the present invention may include a limit on the minimum time ablation energy is delivered. In one embodiment, a minimum energy delivery time is approximately 25 seconds. In another embodiment, a minimum energy delivery time is approximately 40 seconds.

The system of the present invention may include various means of adjusting power levels (delivered) as well as the simultaneous ratio of bipolar to monopolar power delivered. In one embodiment, time division multiplexing (TDM) is utilized to set a power level and/or a bipolar to monopolar ratio.

The system of the present invention may include one or more algorithms which adjust power delivery based on which form of ablation catheters is attached. The power delivery may be adjusted based one or more parameters of the attached ablation catheter, such parameters including but not limited to: distance between two electrodes receiving energy; electrode geometry; thermocouple location; and combinations thereof.

It should be understood that numerous other configurations of the systems, devices and methods described herein can be employed without departing from the spirit or scope of this application. It should be understood that the system includes multiple functional components, such as the RF generator and various ablation catheters of the present invention. In one embodiment, the ablation catheter consists of a catheter shaft, a carrier assembly for providing electrodes in a resiliently biased configuration, a control shaft for deploying and withdrawing the carrier assembly, and a coupler for attaching the control shaft to the carrier assembly. The carrier assembly is a support structure which is shiftable from a storage or confined configuration, such as a radially constrained configuration, to a deployed or expanded configuration. The carrier assembly can include wires, ribbons, cables and struts, made of metals, non-metals or combinations of both. The carrier assembly can be constructed of one or more materials, including both metals and non-metals. Typical metals chosen for carrier assembly construction include but are not limited to: stainless steel, Nitinol, Elgiloy™, other alloys and combinations thereof.

The ablation catheters of the present invention may include a steerable outer sheath, or may work in conjunction as a system with a separate steerable outer sheath. One or more tubular components of the ablation catheter may be steerable such as with the inclusion of a controllable pull wire at or near the distal end. The ablation catheters of the present invention may be inserted over the wire, such as via a lumen within one of the tubular conduits such as within a lumen of the tubular body member or control shaft, or alternatively the catheter may include a rapid exchange sidecar at or near its distal end, consisting of a small projection with a guidewire lumen therethrough. A guidewire lumen may be included solely for the guidewire, or may provide other functions such as a vacuum lumen for an integral suction port integrated at the distal portion of the carrier assembly.

The ablation catheters of the present invention further include one or more ablation elements. In some embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof. The RF generator of the present invention may further provide one of the additional energy forms described immediately hereabove, in addition to the RF energy.

One or more ablation elements may comprise a drug delivery pump or a device to cause mechanical tissue damage such as a forwardly advanceable spike or needle. The ablation elements can deliver energy individually, in combination with or in serial fashion with other ablation elements. The ablation elements can be electrically connected in parallel, in series, individually, or combinations thereof. The ablation catheter may include cooling means, such as fins or other heat sinking geometries, to prevent undesired tissue damage and/or blood clotting. The ablation elements may be constructed of various materials, such as plates of metal and coils of wire for RF energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or an umbrella tip configuration wherein electrodes farthest from the central axis of the catheter have the largest major axis. Wires and other flexible conduits are attached to the ablation elements, such as electrical energy carrying wires for RF electrodes or ultrasound crystals, and tubes for cryogenic delivery.

The ablation catheter of the present invention may include a handle activating or otherwise controlling one or more functions of the ablation catheter. The handle may also include various knobs or levers, such as rotating or sliding knobs which are operably connected to advanceable conduits, or are operably connected to gear trains or cams which are connected to advanceable conduits. These controls, such as knobs use to deflect a distal portion of a conduit, or to advance or retract the carrier assembly, may include a reversible locking mechanism such that a particular tip deflection or deployment amount can be maintained through various manipulations of the system.

The ablation catheter may include one or more sensors, such as sensors used to detect chemical activity; light; electrical activity; pH; temperature; pressure; fluid flow or another physiologic parameter. These sensors can be used to map electrical activity, measure temperature, or gather other information that may be used to modify the ablation procedure. In one embodiment, one or more sensors, such as a mapping electrode, can also be used to ablate tissue.

Numerous components internal to the patient, such as the carrier assembly or electrodes, may include one or more visual markers such as radiopaque markers visible under fluoroscopy, or ultrasound markers.

Selection of the tissue to be ablated may be based on a diagnosis of aberrant conduit or conduits, or based on anatomical location. RF energy may be delivered first, followed by another energy type in the same location, such as when a single electrode can deliver more than one type of energy, such as RF and ultrasound energy. Alternatively or additionally, a first procedure may be performed utilizing one type of energy, followed by a second procedure utilizing a different form of energy. The second procedure may be performed shortly after the first procedure, such as within four hours, or at a later date such as greater than twenty-four hours after the first procedure. Numerous types of tissue can be ablated utilizing the devices, systems and methods of the present invention. For example, the various aspects of the invention have application in procedures for ablating tissue in the prostrate, brain, gall bladder, uterus, other organs and regions of the body, and a tumor, such as regions with an accessible wall or flat tissue surface. In some embodiments, heart tissue is ablated, such as left atrial tissue.

In another embodiment of the system of the present invention, an ablation catheter and a heat sensing technology are included. The heat sensing technology, includes sensor means that may be placed on the chest of the patient, the esophagus or another area in close enough proximity to the tissue being ablated to directly measure temperature effects of the ablation, such as via a temperature sensor, or indirectly such as through the use of an infrared camera. In these embodiments, the RFG includes means of receiving the temperature information from the heat sensing technology, similar to the handling of the temperature information from thermocouples of the ablation catheters. This additional temperature information can be used in one or more algorithms for power delivery, as has been described above, and particularly as a safety threshold which shuts off or otherwise decreased power delivery. A temperature threshold will depend on the location of the heat sensing technology sensor means, as well as where the ablation energy is being delivered. The threshold may be adjustable, and may be automatically configured.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy.

Though the ablation device has been described in terms of an endocardial and transcutaneous method of use, the array may be used on the heart during open heart surgery, open chest surgery, or minimally invasive thoracic surgery. Thus, during open chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A radio frequency energy generation system for delivering radio frequency energy to a cardiac ablation catheter, comprising:
    a radio frequency generator adapted to deliver radio frequency energy in both monopolar and bipolar modes to an ablation catheter, the ablation catheter including an electrode array having at least one electrode, the radio frequency generator including a first output and a second output;
    an EKG monitoring unit adapted to monitor and map signals detected by the at least one electrode, the EKG monitoring unit including a first input from the radio frequency generator and a second input from the radio frequency generator; and
    an interface unit including a first inductor and a second inductor which couple the radio frequency generator and EKG monitoring unit to filter radio frequency signals from EKG signals received by the EKG monitoring unit, the first inductor being located between the first output of the radio frequency generator and the first input of the EKG monitoring unit and the second inductor being located between the second output of the radio frequency generator and the second input of the EKG monitoring unit.

2. The system of claim 1, wherein the at least one electrode is configured to monitor the temperature of atrial tissue adjacent the electrode, and wherein the generator generates radio frequency energy based on the temperature of the atrial tissue.

3. The system of claim 2, wherein the at least one electrode comprises a plurality of electrodes, and wherein the generator is configured to independently monitor the temperature of atrial tissue measured by each of the plurality of electrodes, and wherein the radio frequency generator is configured to generate and deliver radio frequency energy to each of the plurality of electrodes based on the independently monitored temperatures.

4. The system of claim 3, wherein the electrode array includes a first carrier arm, a second carrier arm, a third carrier arm, and a fourth carrier arm.

5. The system of claim 4, wherein the first, second, third, and fourth carrier arms are arranged in an umbrella configuration in which the first, second, third, and fourth carrier arms are approximately 90° from each other.

6. The system of claim 4, wherein the electrode array includes eight electrodes.

7. The system of claim 4, wherein each electrode has a mass of between 17 and 37 milligrams.

8. The system of claim 1, wherein the EKG monitoring unit comprises a plurality of inputs and an inductor associated with each input.

9. The system of claim 1, wherein the generator is configured to deliver energy in a bipolar mode, a monopolar mode, and a combination of both bipolar and monopolar modes.

10. The system of claim 9, wherein the generator is configured to deliver a combination of bipolar and monopolar radio frequency energy to the electrode array in bipolar to monopolar ratios of at least 4:1, 2:1, and 1:1.

11. The system of claim 10, wherein the combination of bipolar and monopolar radio frequency energy is delivered at a constant duty cycle, a constant field length, and a constant bipolar delivery phase angle.

12. The system of claim 11, wherein the field length is 17 msec.

13. The system of claim 11, wherein the phase angle is 90°.

14. The system of claim 13, wherein a ratio of 1:1 bipolar to monopolar energy is achieved by delivering by delivering a first monopolar fields and a second monopolar field, followed by one bipolar field.

15. The system of claim 13, wherein a ratio of 2:1 bipolar to monopolar energy is achieved by delivering one monopolar field followed by one bipolar field.

16. The system of claim 13, wherein a ratio of 4:1 bipolar to monopolar energy is achieved by delivering one monopolar field followed by a first bipolar field and a second bipolar field.

17. A radio frequency energy generation system for delivering radio frequency energy to a cardiac ablation catheter, comprising:
    a radio frequency generator adapted to deliver radio frequency energy in both monopolar and bipolar modes to an ablation catheter, the ablation catheter including an electrode array having at least one electrode configured to monitor the temperature of atrial tissue adjacent the electrode, the generator generating radio frequency energy based at least in part on the temperature of the atrial tissue, the radio frequency generator including a first output and a second output;
    an EKG monitoring unit adapted to monitor and map signals detected by the at least one electrode, the EKG monitoring unit including a first input from the radio frequency generator and a second input from the radio frequency generator, the first and second inputs of the EKG monitoring unit being in electrical communication with the first and second outputs of the radio frequency generator; and an interface unit including a first inductor and a second inductor which couple the radio frequency generator and EKG monitoring unit to filter radio frequency signals from EKG signals received by the EKG monitoring unit, the first inductor being located between the first output of the radio frequency generator and the first input of the EKG monitoring unit and the second inductor being located between the second output of the radio frequency generator and the second input of the EKG monitoring unit.

18. The system of claim 17, wherein the at least one electrode comprises a plurality of electrodes, the generator being adapted to independent monitor the temperature of atrial tissue measured by each of the plurality of electrodes, the generator being configured to generate and deliver radio frequency energy to each of the plurality of electrodes based at least in part on the independently monitored temperatures.

19. The system of claim 18, wherein the generator is configured to deliver a combination of bipolar and monopolar radio frequency energy to the electrode array in bipolar to monopolar ratios of at least 4:1, 2:1, and 1:1.

20. A radio frequency energy generation system for delivering radio frequency energy to a cardiac ablation catheter, comprising:

a radio frequency generator adapted to deliver radio frequency energy in both monopolar and bipolar modes to an ablation catheter, wherein the ablation catheter comprises an electrode array comprising a plurality of electrodes configured to monitor a temperature of atrial tissue adjacent the plurality of electrodes, a first carrier arm, a second carrier arm, a third carrier arm, and a fourth carrier arm, the radio frequency generator generating radio frequency energy based at least in part on the temperature of the atrial tissue, the radio frequency generator including first radio frequency output and a second radio frequency output;

an EKG monitoring unit configured to independently monitor temperature of atrial tissue measured by each of the plurality of electrodes and to map signals detected by each of the plurality of electrodes, the radio frequency generator being configured to generate and deliver radio frequency energy in a monopolar mode, a bipolar mode, and a combination of both bipolar and monopolar modes to each of the plurality of electrodes based at least in part on the independently monitored temperatures, the EKG monitoring unit including an EKG module, the EKG module having a first input and a second input; and an interface unit including a first inductor and a second inductor which couple the radio frequency generator and EKG monitoring unit to filter radio frequency signals from EKG signals received by the EKG monitoring unit, the first inductor being located between the first radio frequency output and the first input of the EKG module and the second inductor being located between the second radio frequency output and the second input of the EKG module, the inductor being a 1000 milliHenry inductor that attenuates a radio frequency energy signal of the radio frequency generator, the interface unit further including a capacitor between the first and second inputs of the EKG module.

* * * * *